(12) United States Patent
Korenaga et al.

(10) Patent No.: US 8,779,133 B2
(45) Date of Patent: Jul. 15, 2014

(54) COMPOUND, NOVEL LIGAND, NOVEL TRANSITION METAL COMPLEX, AND CATALYST INCLUDING NOVEL TRANSITION METAL COMPLEX

(75) Inventors: Toshinobu Korenaga, Okayama (JP); Takashi Sakai, Okayama (JP); Aram Ko, Okayama (JP)

(73) Assignee: National University Corporation Okayama University, Okayama (JP)

( * ) Notice: Subject to any disclaimer, the term of this patent is extended or adjusted under 35 U.S.C. 154(b) by 0 days.

(21) Appl. No.: 13/985,378

(22) PCT Filed: Feb. 16, 2012

(86) PCT No.: PCT/JP2012/053633
§ 371 (c)(1),
(2), (4) Date: Aug. 14, 2013

(87) PCT Pub. No.: WO2012/111737
PCT Pub. Date: Aug. 23, 2012

(65) Prior Publication Data
US 2013/0331576 A1    Dec. 12, 2013

(30) Foreign Application Priority Data
Feb. 17, 2011  (JP) .................................. 2011-031853

(51) Int. Cl.
| C07F 15/00 | (2006.01) |
| C07F 9/00 | (2006.01) |
| C07D 213/04 | (2006.01) |
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |

(52) U.S. Cl.
USPC ................. 546/2; 546/21; 546/255; 546/256; 546/4; 556/21

(58) Field of Classification Search
USPC ............................................................ 546/4
See application file for complete search history.

(56) References Cited

U.S. PATENT DOCUMENTS 5,861,140 A * 1/1999 Peng et al. ................. 424/9.361

FOREIGN PATENT DOCUMENTS

JP  2010173958 A   8/2010
WO 2008120660 A1  10/2008

OTHER PUBLICATIONS

Korenaga; Angew. Chem. Int. Ed. 2011, 50, 10703-10707.*

(Continued)

*Primary Examiner* — John Mabry
*Assistant Examiner* — Daniel Carcanague
(74) *Attorney, Agent, or Firm* — The Webb Law Firm

(57) ABSTRACT

Provided are novel ligands for transition metal complexes which exhibit high coordination power with respect to metals by being free of substituents at the positions ortho to phosphorus or arsenic and which have electron-withdrawing power comparable to the highest level known in conventional ligands. One ligand includes a compound represented by General Formula (1): $R^1R^2R^3A$ or General Formula (2): $R^1R^2A-Y-AR^3R^4$ and having a total of 15 to 110 carbon atoms. In the formulae, A is phosphorus or arsenic; $R^1$, $R^2$, $R^3$ and $R^4$ are each independently a substituted pyridyl group having optionally different electron-withdrawing groups bonded to the positions meta to the atom A as well as hydrogen atoms bonded to the positions ortho to the atom A; and Y is a divalent group derived from a $C_{2\text{-}20}$, optionally substituted and optionally heteroatom-containing, aliphatic, alicyclic or aromatic compound or from ferrocene.

20 Claims, 1 Drawing Sheet

(56) References Cited

OTHER PUBLICATIONS

Korenaga; Adv. Synth. Catal. 2010, 352, 3247-3254.*
Hoge; Chem. Eur. J. 2006, 12, 9025-9035.*
Palo; Organometallics 2000, 19, 81-86.*
Hope; Adv. Synth. Catal. 2006, 348, 1635-1639.*
March; "March's Advanced Organic Chemistry: Reactions, Mechanisms, and Structure", Sixth Edition, 2007 John Wiley & Sons, Chapter 9, pp. 395-416.*
Bowen; Journal of Organometallic Chemistry 554 (1998) 181-184.*
Parks; Journal of Organometallic Chemistry, 1973, 56, 53-66.*
Uchida; Tetrahedron Letters, 1995, 36, 4077-4080.*
Slagt; J. Am. Chem. Soc, 2004, 126, 1526-1536.*

Constable, Edwin C. et al., "Programmed assembly of heteromultinuclear complexes using 4'-diphenylphosphino-2,2':6',2"-terpyridine", Inorganica Chimica Acta 300-302, 2000, pp. 49-55, Elsevier Science S.A.
Korenaga, Toshinobu et al., "Electron-Poor Chiral Diphosphine Ligands: High Performance for Rh-Catalyzed Asymmetric 1,4-Addition of Arylboronic Acids at Room Temperature", Organic Letters, 2009, pp. 2325-2328, vol. 11, No. 11, American Chemical Society.
Korenaga, Toshinobu et al., "Highly Active Rhodium Catalyst With Electeron-Poor Diphosphine Enables Efficient Synthesis of Chiral 4-Aryl-Delta-Lactones", Heterocycles, Aug. 18, 2009, pp. 157-162, vol. 80, No. 1, The Japan Institute of Heterocyclic Chemistry.
Brunner et al.; "Enantioselektive Katalyse; 92. Mitteilung. Optisch aktive Dendrimerphosphine mit verzweigten Pyridinbausteinen"; Synthesis, Jan. 1, 1995, vol. 1995, No. 1, pp. 36-38; XP055109993.

* cited by examiner

BULKINESS EXPERIENCED BY METAL WHEN SUBSTITUENTS ARE INTRODUCED INTO PHOSPHORUS LIGAND

COMPOUND, NOVEL LIGAND, NOVEL TRANSITION METAL COMPLEX, AND CATALYST INCLUDING NOVEL TRANSITION METAL COMPLEX

CROSS-REFERENCE TO RELATED APPLICATIONS

This application is the United States national phase of International Application No. PCT/JP2012/053633 filed Feb. 16, 2012, and claims priority to Japanese Patent Application No. 2011-031853 filed Feb. 17, 2011, the disclosures of which are hereby incorporated in their entirety by reference.

TECHNICAL FIELD

The present invention relates to novel compounds (phosphines and arsines), novel ligands including the compounds, novel transition metal complexes in which the ligands are coordinated to transition metals, and catalysts including the novel transition metal complexes.

BACKGROUND ART

Organometallic complex catalysts have very high utility and potential in the field of organic synthesis chemistry and have found use in cross-coupling reactions which are essential for the development of products such as functional molecules and medicines. The selectivity and the catalytic activity of the metal complex catalysts depend on "ligands" which are coordinated to metals. Because there are no general-purpose ligands exhibiting excellent stereoselectivity and reaction activity in all catalytic reactions, it is necessary that characteristic ligands be identified in order to develop useful catalytic reactions.

Phosphines and arsines are conventional ligands widely used in transition metal complexes. For example, chiral diphosphine compounds represented by BINAP [(1,1-binaphthalene)-2,2-diylbis(diphenylphosphine)] and MeO-BIPHEP [(6,6'-dimethoxybiphenyl-2,2'-diyl)bis(diphenylphosphine)] are used very widely as chiral ligands in optically active transition metal complexes utilized as asymmetric synthesis catalysts.

The present inventors have developed chiral ligands 1a and 1b represented by the formulae below (Patent Literature 1, Non Patent Literatures 1 to 3). Of these ligands, the chiral ligand 1b is "highly electron-deficient", which is an unprecedented characteristic in chiral diphosphine ligands, and is a very promising ligand that can give metal catalysts capable of catalyzing an asymmetric 1,4-addition reaction with high enantioselectivity and with the world's highest activity achieved in catalytic asymmetric carbon-carbon bond formation reactions.

[Chem. 1]

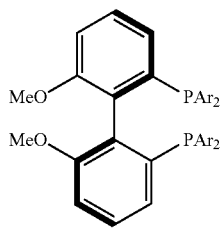

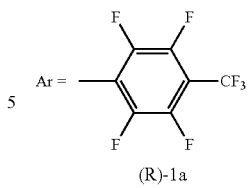

(R)-1a

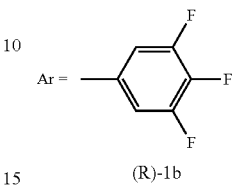

(R)-1b

CITATION LIST

Patent Literature

Patent Literature 1: JP-A-2010-173958

Non Patent Literature

Non Patent Literature 1: Org. Lett. 2009, 11, 2325.
Non Patent Literature 1: Adv. Synth. Catal. 2010, 352, 3247.
Non Patent Literature 2: Heterocycles 2010, 80, 157.

Basically, the electron-withdrawing power of an aromatic ring increases with increasing number of fluorine atoms on the aromatic ring. Thus, the chiral ligand 1a having a perfluoro aromatic ring (an aromatic ring in which the hydrogen atoms at all the positions except for the bond to carbon are substituted by fluorine atoms) such as a heptafluorotolyl group or a pentafluorophenyl group is more electron-deficient than the ligand 1b. However, while metal complexes having the ligands 1b exhibited high activity, those having the more electron-deficient ligands 1a failed to achieve good catalytic activity. The reason for this is probably because the ortho fluorine atoms in the ligand 1a increase the bulkiness around the phosphorus atom to make it difficult for the ligand 1a to be coordinated to the metal (FIG. 1).

The present invention has an object of providing novel ligands for transition metal complexes which exhibit high coordination power with respect to metals by being free of substituents at the positions ortho to phosphorus or arsenic and which are comparable to the ligand 1a in terms of electron-withdrawing power (electron deficiency).

SUMMARY OF THE INVENTION

The present inventors have found that bistrifluoromethyl-pyridyl groups (2) can form a phosphine ligand capable of solving the aforementioned problems which has electron-withdrawing power comparable to that of the ligand 1a and which exhibits strong coordination power with respect to a metal because the bulkiness experienced by the metal is small (FIG. 2). The present inventors have then synthesized several types of novel phosphine compounds having such groups. Further, the inventors have confirmed that transition metal complexes having such phosphine ligands practically outperform transition metal complexes having the chiral ligands 1b in terms of catalytic activity. The present invention has been completed based on these findings.

That is, the present invention provides a compound represented by General Formula (1) or (2) and having a total of 15 to 110 carbon atoms:

R¹R²R³A         (1)

R¹R²A-Y-AR³R⁴   (2)

(wherein A is phosphorus or arsenic; $R^1$, $R^2$, $R^3$ and $R^4$ are each independently a substituted pyridyl group having optionally different electron-withdrawing groups bonded to the positions meta to the atom A as well as hydrogen atoms bonded to the positions ortho to the atom A; and Y is a divalent group derived from a $C_{2-20}$, optionally substituted and optionally heteroatom-containing, aliphatic, alicyclic or aromatic compound or from ferrocene).

The electron-withdrawing group is preferably at least one selected from the group consisting of a perhaloalkyl group having 1 to 4 carbon atoms, a halogen, nitro group, cyano group, pentafluorophenyl group, tetrafluoropyridyl group, heptafluorotolyl group, 2,6-ditrifluoromethylpyridyl group and 3,5-ditrifluoromethylphenyl group. For example, the perhaloalkyl group having 1 to 4 carbon atoms may be at least one selected from the group consisting of a perfluoroalkyl group, a perchloroalkyl group and a perbromoalkyl group each having 1 to 4 carbon atoms. In more detail, the perfluoroalkyl group having 1 to 4 carbon atoms is preferably at least one selected from the group consisting of trifluoromethyl group, pentafluoroethyl group, heptafluoropropyl group and nanofluorobutyl group. The halogen may be at least one selected from the group consisting of fluorine, chlorine, bromine and iodine.

Specific examples of the compounds represented by General Formula (1) include tri[2,6-bis(trifluoromethyl)-4-pyridyl]phosphine, tri[2,6-bispentafluoroethyl-4-pyridyl]phosphine, tri[2,6-bisheptafluoropropyl-4-pyridyl]phosphine, tri[2,6-bisnanofluorobutyl-4-pyridyl]phosphine, tri[2,6-difluoro-4-pyridyl]phosphine, tri[2,6-dinitro-4-pyridyl]phosphine and tri[2,6-dicyano-4-pyridyl]phosphine.

Specific examples of the compounds represented by General Formula (2) include compounds represented by Formula (4), (5) or (6) below:

[Chem. 2]

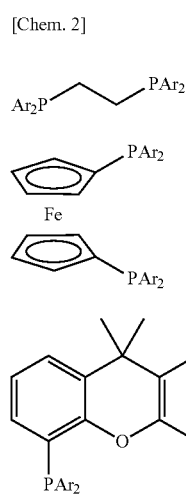

(4)

(5)

(6)

(wherein Ar is 2,6-bistrifluoromethyl-4-pyridyl group).

Further, examples of the compounds represented by General Formula (2) include compounds represented by General Formula (7) below, and in more detail axially chiral compounds represented by Formula (10), (11), (12) or (13) below:

[Chem. 3]

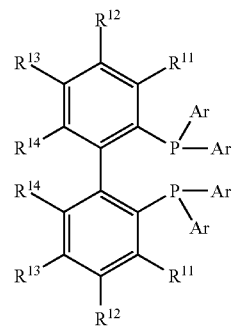

(7)

(wherein $R^{11}$, $R^{12}$ and $R^{13}$ are each independently a hydrogen atom, a halogen atom, an alkyl group having 1 to 6 carbon atoms, an alkoxy group having 1 to 6 carbon atoms, a fluorinated alkyl group having 1 to 10 carbon atoms, or a fluorinated alkoxy group having 1 to 10 carbon atoms; $R^{14}$ is an alkyl group having 1 to 6 carbon atoms, a fluorinated alkyl group having 1 to 10 carbon atoms, an alkoxy group having 1 to 6 carbon atoms, or a fluorinated alkoxy group having 1 to 10 carbon atoms; and $R^{11}$, $R^{12}$, $R^{13}$ and $R^{14}$ on the same benzene ring may be linked to one another to form a ring);

[Chem. 4]

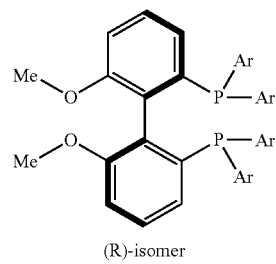

(10)

(R)-isomer

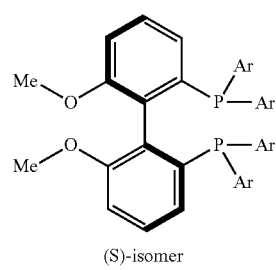

(11)

(S)-isomer

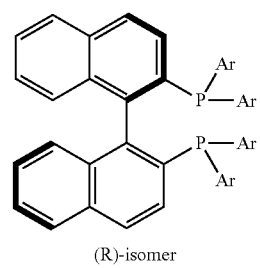

(12)

(R)-isomer

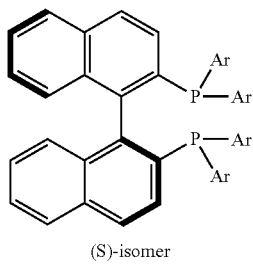

(13)

(S)-isomer

The invention further provides ligands including the aforementioned compounds, and transition metal complexes in which the ligands are coordinated to transition metals having coordination capability.

Examples of the transition metals having coordination capability include titanium, vanadium, manganese, iron, cobalt, nickel, copper, zirconium, niobium, molybdenum, ruthenium, rhodium, palladium, hafnium, tantalum, tungsten, rhenium, osmium, iridium, silver, gold and platinum.

Further, the invention provides catalysts including the transition metal complexes. Examples of the catalysts include chiral catalysts represented by Formula (17) below:

[RhCl(C$_2$H$_4$)$_2$]$_2$/(R)-L*  (17)

(wherein (R)-L* indicates a chiral bidentate ligand formed by an axially chiral compound represented by Formula (10)).

The novel ligands provided according to the invention have the highest electron-withdrawing properties among aromatic phosphines (P—Ar) and are easily coordinated to metal catalysts because the ligands are not sterically bulky due to the absence of ortho substituents inhibiting the coordination to metals. This means that the ligands exert unprecedented and sufficient electronic influences on metals to which they are coordinated and thereby allow for marked improvements in catalytic activity. Indeed, as will be described in Examples later, the PAr$_3$ ligands have been demonstrated to realize higher catalytic activity in a cross-coupling reaction (the Stille coupling) than achieved with conventional ligands. Further, the chiral diphosphine ligands have been demonstrated to realize far higher catalytic activity in the asymmetric arylation of imines than conventional chiral catalysts while maintaining high enantioselectivity. This will lead to efficient synthesis of optically active amino compounds which are essential in medicines. These facts not only show that the ligands have superiority in these reactions but also indicate that the ligands are very potential and possibly promise the realization of the high functionalization of catalysts and the development of new (asymmetric) catalytic reactions.

DESCRIPTION OF EMBODIMENTS

Figure 1:
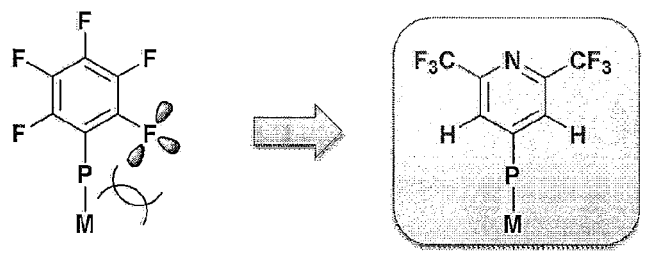
FIG. 1 is a view illustrating how the stability of a phosphorus-metal bond is affected by the substituents ortho to the phosphorus in a conventional ligand having a pentafluorophenyl group and an inventive ligand having a bis(trifluoromethyl)pyridyl group. (Left) The bulky fluorine atoms at the ortho positions destabilize the phosphorus (P)-metal (M) bond. (Right) The phosphine having a nonbulky and highly electron-withdrawing bistrifluoromethyl-pyridyl group exhibits high coordination capability with respect to the metal.
Figure 2:
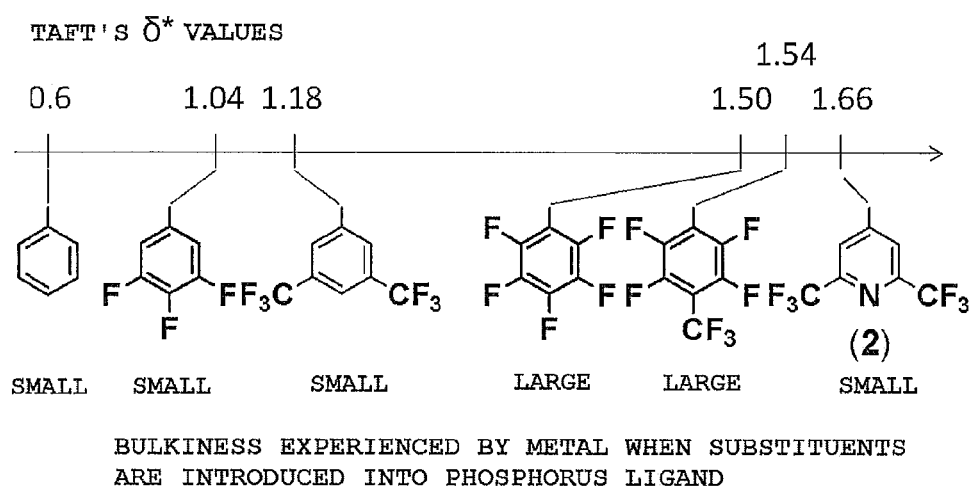
FIG. 2 illustrates Taft's δ* values of substituents in conventional ligands and an inventive ligand (larger values indicate higher electron-withdrawing properties), as well as the degrees of bulkiness experienced by a metal when the substituents are introduced into a phosphorus ligand.

In the following part of the specification, "compounds represented by General Formula (n)" (n is a natural number) or ligands including the compounds may be referred to as "compounds (n)" or "ligands (n)". The substituents corresponding to R$^1$, R$^2$, R$^3$ and R$^4$ in Formula (1) or Formula (2) may be represented by the symbol "Ar".

—Novel Compounds—

A first novel compound of the invention is represented by General Formula (1) below and has a total of 15 to 110 carbon atoms.

R$^1$R$^2$R$^3$A  (1)

In Formula (1), A is phosphorus or arsenic; and R$^1$, R$^2$ and R$^3$ are each independently a substituted pyridyl group having optionally different electron-withdrawing groups bonded to the positions meta to the atom A as well as hydrogen atoms bonded to the positions ortho to the atom A.

A second novel compound of the invention is represented by General Formula (2) below and has a total of 15 to 110 carbon atoms.

R$^1$R$^2$A-Y-AR$^3$R$^4$  (2)

In Formula (2), A is phosphorus or arsenic; R$^1$, R$^2$, R$^3$ and R$^4$ are each independently a substituted pyridyl group having optionally different electron-withdrawing groups bonded to the positions meta to the atom A as well as hydrogen atoms bonded to the positions ortho to the atom A; and Y is a divalent group derived from a C$_{2-20}$, optionally substituted and optionally heteroatom-containing, aliphatic, alicyclic or aromatic compound or from ferrocene.

Provided that the nitrogen atom in the pyridine ring has the lowest number (1-position), the positions meta to the atom A are the 2-position and the 6-position, and electron-withdrawing groups which may be different from each other are bonded to these positions. Provided that the nitrogen atom in the pyridine ring has the lowest number (1-position), the positions ortho to the atom A are the 3-position and the 5-position, and hydrogen atoms are bonded to these positions.

Examples of the "electron-withdrawing groups" present in R$^1$, R$^2$, R$^3$ and R$^4$ in Formulae (1) and (2) include, but are not limited to, perhaloalkyl groups having 1 to 4 carbon atoms, halogens, nitro group, cyano group, pentafluorophenyl group, tetrafluoropyridyl group, heptafluorotolyl group, 2,6-ditrifluoromethylpyridyl group and 3,5-ditrifluoromethylphenyl group. The "electron-withdrawing groups" in the invention may be generally any substituents which have stronger electron-withdrawing power than the unsubstituted phenyl group. Appropriate groups may be selected from such electron-withdrawing groups and may be introduced onto pyridine rings to form R$^1$, R$^2$, R$^3$ and R$^4$.

Of the "electron-withdrawing groups", examples of the "perhaloalkyl groups having 1 to 4 carbon atoms" include perfluoroalkyl groups, perchloroalkyl groups and perbromoalkyl groups each having 1 to 4 carbon atoms.

Examples of the "perfluoroalkyl groups having 1 to 4 carbon atoms" include trifluoromethyl group, pentafluoroethyl group, heptafluoropropyl group and nanofluorobutyl group.

Of the "electron-withdrawing groups", examples of the "halogens" include fluorine, chlorine, bromine and iodine.

In particular, the 2,6-bis(trifluoromethyl)-4-pyridyl group is a suitable electron-withdrawing group in the invention because sufficiently high catalytic activity can be obtained, the preparation of phosphine or arsine is easy, the materials for the group are available relatively easily, and this group has the highest level of electron-withdrawing power among aromatic rings.

Specific examples of the compounds (1) include tri[2,6-bistrifluoromethyl-4-pyridyl]phosphine, tri[2,6-bispentafluoroethyl-4-pyridyl]phosphine, tri[2,6-bisheptafluoropropyl-4-pyridyl]phosphine, tri[2,6-bisnanofluorobutyl-4-pyridyl]phosphine, tri[2,6-difluoro-4-pyridyl]phosphine, tri [2,6-dinitro-4-pyridyl]phosphine and tri[2,6-dicyano-4-pyridyl]phosphine.

Referring to Formula (2), Y represents a "divalent group derived from a $C_{2-20}$, optionally substituted and optionally heteroatom-containing, aliphatic, alicyclic or aromatic compound or from ferrocene". This group may be selected from divalent groups in known phosphines/arsines (having known functional groups corresponding to $R^1$, $R^2$, $R^3$ and $R^4$ in Formula (2) of the invention) capable of forming complexes by being coordinated to transition metals, wherein the divalent groups are at sites corresponding to Y in Formula (2) of the invention.

Typical examples of the compounds (2) include compounds of Formula (7) below in which Y is a divalent group with a biphenyl skeleton.

[Chem. 5]

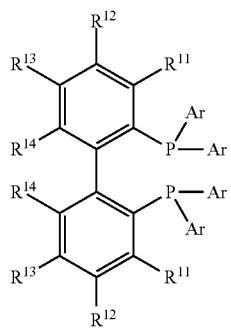

(7)

In Formula (7), $R^{11}$, $R^{12}$ and $R^{13}$ are each independently a hydrogen atom, a halogen atom, an alkyl group having 1 to 6 carbon atoms, an alkoxy group having 1 to 6 carbon atoms, a fluorinated alkyl group having 1 to 10 carbon atoms, or a fluorinated alkoxy group having 1 to 10 carbon atoms; $R^{14}$ is an alkyl group having 1 to 6 carbon atoms, a fluorinated alkyl group having 1 to 10 carbon atoms, an alkoxy group having 1 to 6 carbon atoms, or a fluorinated alkoxy group having 1 to 10 carbon atoms; and $R^{11}$, $R^{12}$, $R^{13}$ and $R^{14}$ on the same benzene ring may be linked to one another to form a ring.

Examples of the halogen atoms include fluorine, chlorine and bromine atoms. Examples of the alkyl groups having 1 to 6 carbon atoms include methyl group, ethyl group, 1-propyl group, 2-propyl group, 1-butyl group, 2-butyl group, 2-methyl-2-propyl group, 1-pentyl group and 1-hexyl group. Examples of the alkoxy groups having 1 to 6 carbon atoms include methoxy group, ethoxy group, 1-propoxy group, 2-propoxy group, 1-butoxy group, 2-butoxy group, 2-methyl-2-propoxy group, 1-pentyloxy group and 1-hexyloxy group.

Examples of the fluorinated alkyl groups having 1 to 10 carbon atoms include alkyl groups in which all the hydrogen atoms are substituted by fluorine atoms (perfluoroalkyl groups), and alkyl groups in which part of the hydrogen atoms are substituted by fluorine atoms. These groups may be linear or branched. When this diphosphine compound of the invention is used as a ligand of a catalyst in an asymmetric synthesis reaction involving a fluorine-containing solvent, the catalyst can exhibit good solubility. Examples of the fluorinated alkyl groups include those represented by Formula (8) below.

(8)

In Formula (8), the letter m is an integer of 1 to 9, the letter n is an integer of 0 to 8, and m+n is an integer of 1 to 9.

Examples of the fluorinated alkoxy groups having 1 to 10 carbon atoms include alkoxy groups in which all the hydrogen atoms are substituted by fluorine atoms (perfluoroalkoxy groups), and alkoxy groups in which part of the hydrogen atoms are substituted by fluorine atoms. These groups may be linear or branched. When this diphosphine compound of the invention is used as a ligand of a catalyst in an asymmetric synthesis reaction involving a fluorine-containing solvent, the catalyst can exhibit good solubility. Examples of the fluorinated alkoxy groups include those represented by Formula (9) below.

(9)

In Formula (9), the letter m is an integer of 1 to 9, the letter n is an integer of 0 to 8, and m+n is an integer of 1 to 9.

Because of easy synthesis, it is preferable that $R^{11}$, $R^{12}$ and $R^{13}$ be all hydrogen atoms.

The synthesis of the compound is easy when $R^{14}$s bonded at the 6-position and the 6'-position of the biphenyl skeleton are alkoxy groups. In particular, the synthesis is advantageously easy when $R^{14}$s are methyl groups, that is, when methoxy groups are bonded at the 6-position and the 6'-position of the biphenyl skeleton.

$R^{11}$, $R^{12}$, $R^{13}$ and $R^{14}$ bonded to the same benzene ring may be linked to one another to form a ring. As a preferred example of such groups, $R^{13}$ and $R^{14}$ which are both alkyl groups and have a total of 4 carbon atoms are bonded to each other and form a naphthalene ring in combination with the already present benzene ring. For example, compounds (5) and (6) have such preferred groups.

The groups Y having a biphenyl skeleton or a binaphthalene skeleton are axially chiral optical isomers. From the viewpoint of easy preparation of a target metal complex (an asymmetric synthesis catalyst), the compound (2) having such a group Y is desirably prepared in an optically active form which is an R-isomer or an S-isomer. Alternatively, the compound (2) may be prepared as a racemic isomer (a mixture of equal amounts of an R-isomer and an S-isomer) and may be optically resolved at an appropriate stage, for example, after the compound is coordinated to a transition metal to form a complex, thus obtaining a final target asymmetric synthesis catalyst.

Specific examples of phosphines corresponding to the inventive compounds (1) or (2) are illustrated below.

[Chem. 6]

Achiral phosphines

(3)

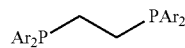

(4)

-continued

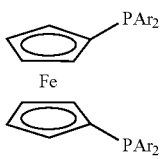

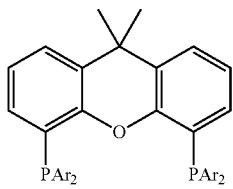

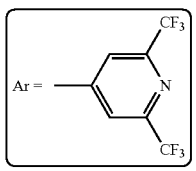

Chiral phosphines (10)

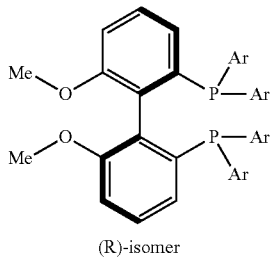

(R)-isomer (11)

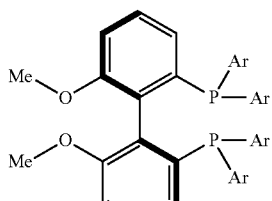

(S)-isomer (12)

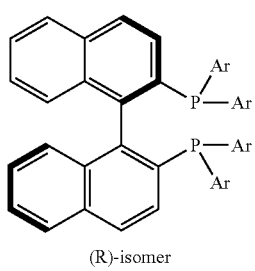

(R)-isomer (5)

(6)

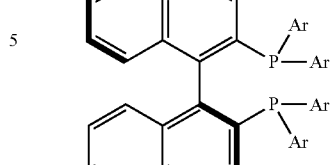

(S)-isomer (13)

In Formulae (10), (11), (12) and (13), Me indicates a methyl group and Ar indicates a 2,6-bis(trifluoromethyl)-4-pyridyl group.

—Methods for Producing Novel Compounds—

The novel compounds of the invention may be synthesized by methods similar to those for producing conventional phosphines or arsines, except that the specific substituted pyridyl groups are introduced.

For example, a phosphine compound of the invention (represented by General Formula (1) in which A is phosphorus) may be suitably synthesized by a method (a Grignard reaction) including:

a first step of reacting a compound represented by General Formula (14) below with magnesium and a lithium halide, and a second step of reacting the reaction product from the first step (a Grignard reagent) with a halogenated phosphorus compound represented by General Formula (15) or General Formula (16) below.

$$R-X^1 \qquad (14)$$

In Formula (14), R has the same meaning as $R^1$, $R^2$, $R^3$ and $R^4$ in General Formula (1) or (2), and $X^1$ is a halogen atom.

$$P-X^2{}_3 \qquad (15)$$

$$X^2{}_2P-Y-PX^2{}_2 \qquad (16)$$

In Formulae (15) and (16), $X^2$ is a halogen atom and Y has the same meaning as in General Formula (2).

The first step prepares a Grignard reagent to be used in the subsequent second step. The compound (14) is selected such that the functional groups R correspond to $R^1$, $R^2$, $R^3$ and $R^4$ in the target compound (1) or (2). Preferably, $X^1$ in the compound (14) is bromine. The compound (14) as a material may be prepared in accordance with a known method or may be commercially purchased.

In the second step, the target compound is synthesized by a Grignard reaction using the Grignard reagent prepared in the first step. Preferably, $X^2$ in the compounds (15) and (16) is chlorine. The compounds (15) and (16) as materials may be prepared in accordance with a known method or may be commercially purchased.

The Grignard reagent prepared in the first step is difficult to isolate. Thus, the first step and the second step are usually performed continuously in such a manner that the compound (15) or (16) used in the second step is added to the reaction system from the first step.

Similarly to the usual Grignard reaction, the reaction solvent used in the first step and the second step is an anhydrous aprotic organic solvent. Ethers such as tetrahydrofuran (THF) and diethyl ether are preferred. Other reaction conditions such as the reaction temperature, the reaction time, and the amount of the compound (14) used relative to the compound (15) or (16) may be adjusted appropriately depending on the type of the target compound (1) or (2) in accordance with conventional methods. Usually, the reaction temperature is room temperature to 60° C., the reaction time is 1 to 8 hours, and the amount of the compound (14) used is 1.5 to 3 moles per 1 mole of phosphorus atoms.

By adopting the preparation method described above, the target compound (2) may be obtained without the occurrence of racemization even in the case where the compound (16) has a divalent group Y formed by an axially chiral compound.

—Novel Transition Metal Complexes—

The novel compounds of the invention described above act as ligands that bond to transition metals having coordination capability. The transition metal complexes of the invention are formed by the coordination of such ligands to transition metals having coordination capability.

Examples of the transition metals (elements in Groups III to XI in the periodic table) having coordination capability include titanium, vanadium, manganese, iron, cobalt, nickel, copper, zirconium, niobium, molybdenum, ruthenium, rhodium, palladium, hafnium, tantalum, tungsten, rhenium, osmium, iridium, silver, gold and platinum. Of these, the elements of Groups VIII, IX and X in the periodic table such as rhodium, platinum, palladium, ruthenium, nickel, iron and iridium are preferable. When these transition metals are used, it is preferable that the inventive novel compounds be coordinated to transition metal salts or transition metal complexes such as halides, carbonyl complexes, olefin complexes and enolate complexes.

The transition metal complexes of the invention may be prepared by methods similar to those for producing known transition metal complexes. In a usual method, the novel compound of the invention (a phosphine or an arsine) may be mixed together with a transition metal compound in an appropriate solvent so as to form a complex in the reaction system. The resultant transition metal complex may be used as it is without being separated from the reaction system used for the preparation, or may be used after separated therefrom and purified as required.

The transition metal complexes of the invention may be used as catalysts in reactions usually catalyzed by known transition metal complexes. For example, transition metal complexes having the inventive axially chiral phosphine compounds as the ligands may be used as chiral catalysts in various asymmetric synthesis reactions such as asymmetric hydrogenation reactions (such as reduction of ketones, and reduction of imines), asymmetric addition reactions (such as 1,4-addition reaction and 1,2-addition reaction), asymmetric isomerization reactions (such as olefin isomerization), and asymmetric cross-coupling reactions (such as the Suzuki-Miyaura coupling reaction). In addition to these asymmetric synthesis reactions, the inventive transition metal complexes may be used in various reactions usually catalyzed by known transition metal complexes (such as the Stille coupling reaction and the Heck reaction). In other words, the scope of the present invention includes the use of the novel transition metal complexes as catalysts in the above reactions as well as the methods of performing the above reactions by utilizing the novel transition metal complexes as catalysts.

As an example, a chiral catalyst represented by General Formula (17) may be used in the asymmetric arylation of imines which can synthesize optically active amines found in large amounts in substances such as bioactive substances.

(17)

In Formula (17), (R)-L indicates a chiral bidentate ligand formed by an axially chiral compound represented by General Formula (10).

The amount of the inventive transition metal catalyst used may be adjusted appropriately in accordance with the type of the reaction catalyzed or the catalyst used. However, the amount of the catalyst is usually 0.5 to 3 mol %, and preferably 0.1 to 0.5 mol % relative to material compounds. Because the transition metal catalysts of the invention exhibit very high catalytic activity compared to conventional catalysts, the amount thereof may be smaller than the conventional level. Reaction conditions such as reaction temperature and reaction time may be adjusted appropriately. However, milder temperature conditions and shorter reaction time than the conventional conditions may be adopted because of the high catalytic activity of the inventive transition metal catalysts.

EXAMPLES

Example 1-1

[Chem. 7]

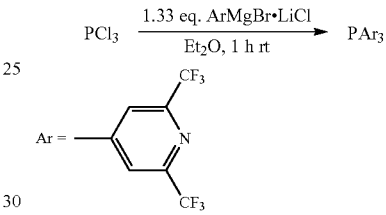

A thoroughly dried 50 mL two-necked recovery flask was charged with magnesium turnings (365 mg, 15.0 mmol) and lithium chloride (318 mg, 7.49 mmol). In an inert gas atmosphere, Et$_2$O (20 mL) was added. Next, a hexane solution of DAIBAL-H (1 M, 100 μL, 0.100 mmol) was added dropwise, and the mixture was stirred for 5 minutes. Thereafter, 4-bromo-2,6-bis(trifluoromethyl)pyridine (1.77 g, 6.00 mmol) was added, and the mixture was stirred for 1 hour. Further, trichlorophosphine (131 μL, 1.5 mmol) was added dropwise over a period of about 5 minutes, and the reaction was carried out for 1 hour. The reaction was then terminated by the addition of a saturated aqueous ammonium chloride solution, and Et$_2$O was distilled away. The residue was dissolved in ethyl acetate to perform extraction. The extracted phase was washed with a saturated aqueous sodium chloride solution, filtered through Celite, and concentrated to dryness. The product was purified by silica gel column chromatography (hexane/ethyl acetate=6/1) to give a target compound (78% yield). $^1$H NMR (300 MHz, acetone-d$_6$): δ 8.48 (d, J=6.6 Hz). $^{19}$F NMR (282 MHz, acetone-d$_6$): δ −64.5 (s). $^{31}$P NMR (121 MHz, acetone-d$_6$): δ 0.17 (s). IR (KBr): 3069, 1722, 1593, 1454, 1361, 1283, 1198, 1150, 1103, 901, 854, 718, 696, 683 cm$^{-1}$. Anal. calc. for C$_{21}$H$_6$F$_{18}$N$_3$P: C, 37.46; H, 0.90; N, 6.24. Found: C, 37.39; H, 1.26; N, 6.37.

Example 1-2

[Chem. 8]

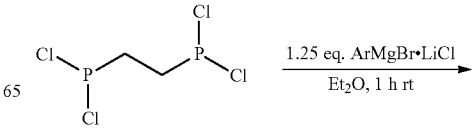

-continued

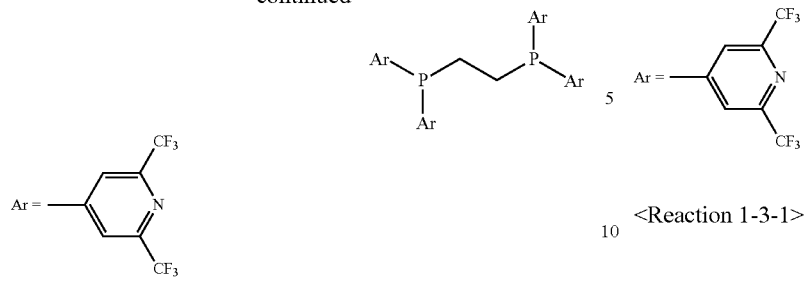

-continued

<Reaction 1-3-1>

A thoroughly dried 50 mL two-necked recovery flask was charged with magnesium turnings (365 mg, 15.0 mmol) and lithium chloride (318 mg, 7.49 mmol). In an inert gas atmosphere, Et$_2$O (20 mL) was added. Next, a hexane solution of DAIBAL-H (1 M, 100 μL, 0.100 mmol) was added dropwise, and the mixture was stirred for 5 minutes. Thereafter, 4-bromo-2,6-bis(trifluoromethyl)pyridine (1.77 g, 6.00 mmol) was added, and the mixture was stirred for 1 hour. Further, bis(dichlorophosphino)ethane (150 μL, 1.0 mmol) was added dropwise over a period of about 5 minutes, and the reaction was carried out for 1 hour. The reaction was then terminated by the addition of a saturated aqueous ammonium chloride solution, and Et$_2$O was distilled away. The residue was dissolved in ethyl acetate to perform extraction. The extracted phase was washed with a saturated aqueous sodium chloride solution, filtered through Celite, and concentrated to dryness. The product was purified by silica gel column chromatography (hexane/ethyl acetate=5/1) to give a target compound (81% yield). $^1$H NMR (300 MHz, acetone-d$_6$): δ 2.96 (t, J=5.1 Hz, 4H), 8.28-8.30 (m, 8H). $^{19}$F NMR (282 MHz, acetone-d$_6$): δ −64.5 (s). $^{31}$P NMR (121 MHz, acetone-d$_6$): δ −3.24 (s). IR (KBr): 1593, 1454, 1361, 1288, 1205, 1134, 899, 854, 718, 696, 683 cm$^{-1}$. Anal. calc. for C$_{30}$H$_{12}$F$_{24}$N$_4$P$_2$: C, 38.07; H, 1.28; N, 5.92. Found: C, 37.69; H, 1.28; N, 6.17.

Example 1-3

Synthesis Scheme (Reactions 1-3-1 to 1-3-3 Described Below)

[Chem. 9]

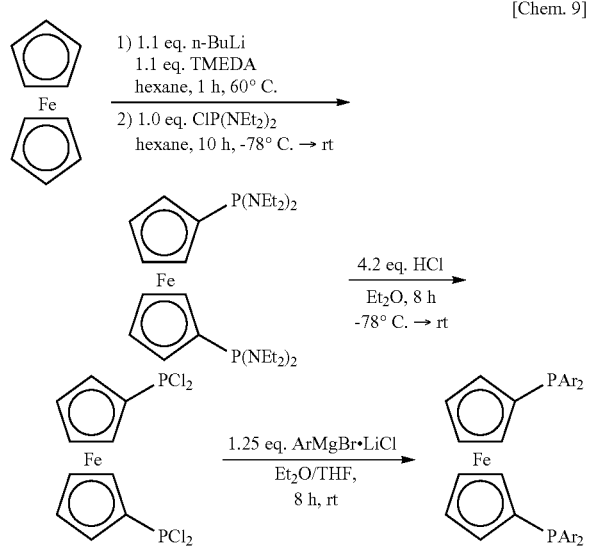

[Chem. 10]

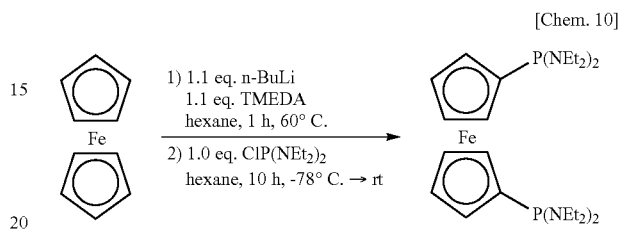

A thoroughly dried 50 mL Schlenk tube was charged with ferrocene (279 mg, 1.50 mmol). In an inert gas atmosphere, N,N,N',N'-tetramethyl-1,2-ethanediamine (490 μL, 3.3 mmol) and hexane (12 mL) were added. Further, 1.59 M n-butyllithium (2.1 mL, 3.3 mmol) was added dropwise over a period of about 10 minutes, and the mixture was stirred at 60° C. for 1 hour. The mixture was then cooled to −78° C., and a hexane (3 mL) solution of bis(diethylamino)chlorophosphine (620 μL, 2.9 mmol) and triethylamine (400 μL, 2.9 mmol) was added dropwise over a period of about 10 minutes. The reaction liquid was stirred at room temperature for 10 hours and was filtered through Celite in an inert gas atmosphere. After the solvent was distilled away, the residue was subjected to Reaction 1-3-2 without further purification. $^1$H NMR (300 MHz, C$_6$D$_6$): δ 1.04 (t, J=6.8 Hz, 24H), 3.00-3.10 (m, 16H), 4.39-4.43 (m, 8H). $^{31}$P NMR (121 MHz, C$_6$D$_6$): δ 91.3 (s).

<Reaction 1-3-2>

[Chem. 11]

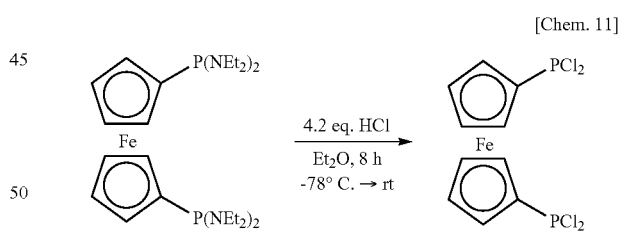

In an inert gas atmosphere, a thoroughly dried 50 mL Schlenk tube was charged with a Et$_2$O solution (4 mL) of 1,1'-bis[bis[diethylamino]phosphino]ferrocene synthesized in [3]. The solution was cooled to −78° C. A Et$_2$O solution of hydrogen chloride (1 M, 25 mL, 25 mmol) was added dropwise over a period of about 20 minutes. The mixture was then stirred for 8 hours while gradually increasing the temperature to room temperature. The solvent was distilled away. In an inert gas atmosphere, benzene was added to dissolve the salts formed by the reaction, the salts being removed by Celite filtration. After the solvent was distilled away, the residue was subjected to Reaction 1-3-3 without further purification. $^1$H NMR (300 MHz, C$_6$D$_6$): δ 3.98 (t, J=1.9 Hz, 4H), 4.15-4.18 (m, 4H). $^{31}$P NMR (121 MHz, C$_6$D$_6$): δ 162.6 (s).

15

<Reaction 1-3-3>

[Chem. 12]

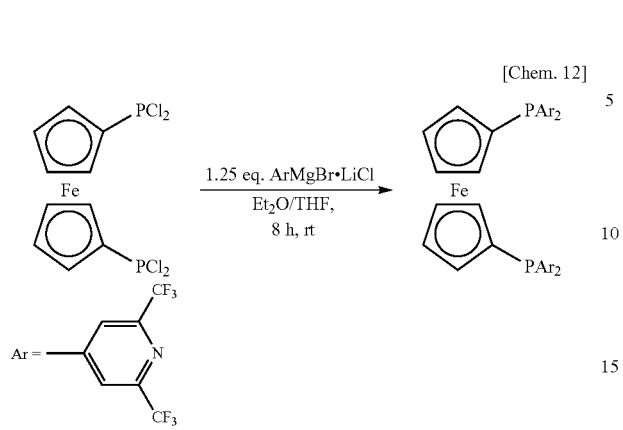

A thoroughly dried 50 mL two-necked recovery flask was charged with magnesium turnings (457 mg, 18.8 mmol) and lithium chloride (399 mg, 9.41 mmol). In an inert gas atmosphere, Et$_2$O (20 mL) was added. Next, a hexane solution of DAIBAL-H (1 M, 120 µL, 0.120 mmol) was added dropwise, and the mixture was stirred for 5 minutes. Thereafter, 4-bromo-2,6-bis[trifluoromethyl]pyridine (2.20 g, 7.50 mmol) was added, and the mixture was stirred for 1 hour. Further, a THF solution (5 mL) of 1,1'-bis(dichlorophosphino)ferrocene synthesized in Reaction 1-3-2 was added dropwise over a period of about 10 minutes, and the reaction was carried out for 8 hours. The reaction was then terminated by the addition of a saturated aqueous ammonium chloride solution, and THF was distilled away. The residue was dissolved in ethyl acetate to perform extraction. The extracted phase was washed with a saturated aqueous sodium chloride solution, filtered through Celite, and concentrated to dryness. The product was purified by silica gel column chromatography (hexane/ethyl acetate=3/1) to give a target compound (35% yield (3 stages)). $^1$H NMR (300 MHz, CDCl$_3$): δ 3.98-4.02 (m, 4H), 4.42-4.46 (m, 4H), 7.69 (d, J=6.3 Hz, 8H), 7.89 (s, 4H). $^{13}$C NMR (75 MHz, acetone-d$_6$): δ 71.5 (d, J=6.8 Hz), 74.7 (d, J=4.1 Hz), 75.5 (d, J=16.1 Hz), 121.9 (q, J=272.9 Hz), 128.7 (d, J=17.9 Hz), 148.6 (dq, J=5.6, 35.7 Hz), 153.5 (d, J=22.6 Hz). $^{19}$F NMR (282 MHz, CDCl$_3$): δ −64.6 (s). $^{31}$P NMR (121 MHz, CDCl$_3$): δ −15.0 (s). IR (KBr): 3050, 1593, 1362, 1283, 1200, 1144, 1124, 897, 854, 835, 720, 696 cm$^{-1}$. M.p.=240° C. (dec.) Anal. calc. for C$_{38}$H$_{16}$F$_{24}$FeN$_4$P$_2$: C, 41.40; H, 1.46; N, 5.08. Found: C, 41.28; H, 1.71; N, 4.68.

Example 1-4

Synthesis Scheme (Reactions 1-4-1 to 1-4-6 Described Below)

[Chem. 13]

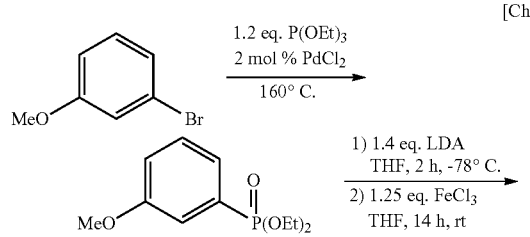

16

-continued

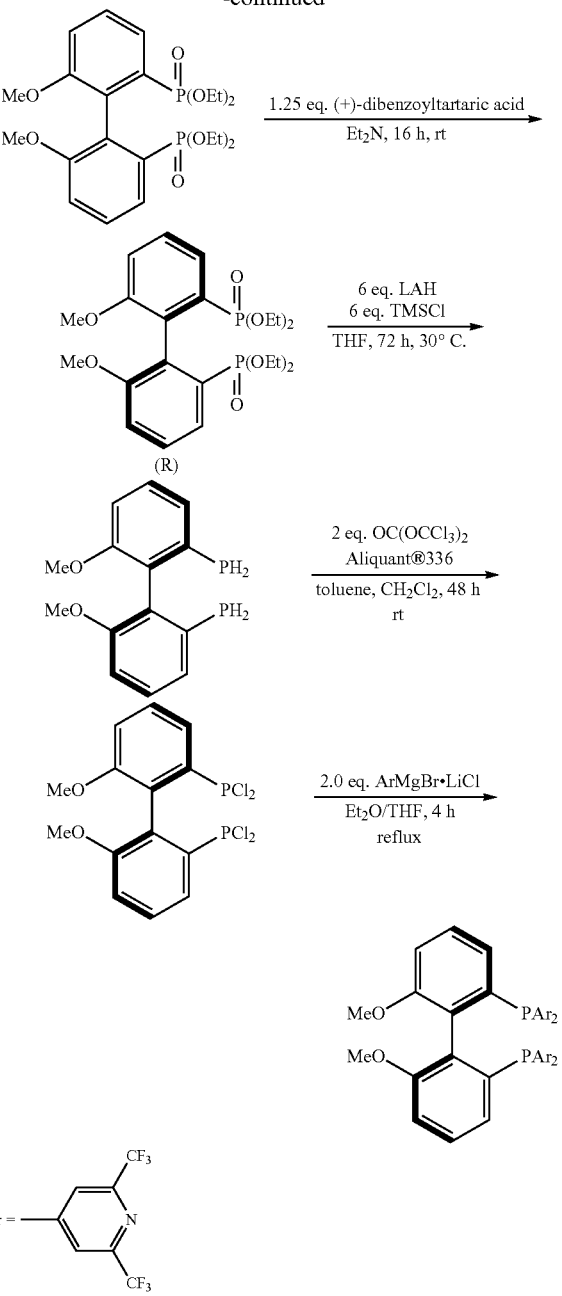

<Reaction 1-4-1>

[Chem. 14]

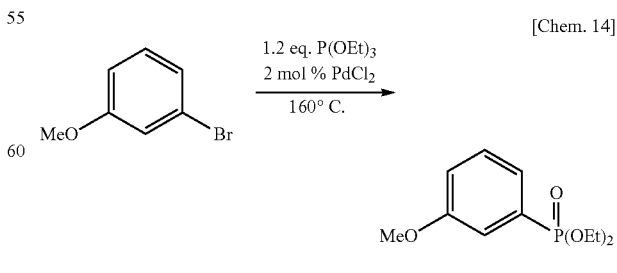

In an inert gas atmosphere, a thoroughly dried 50 mL two-necked recovery flask was charged with palladium (II)

chloride (485 mg, 2.70 mmol) and 3-bromoanisole (17 mL, 134 mmol). While performing stirring at 160° C., a total of 28 mL (160 mmol) of triethyl phosphite was added by adding an approximately 5 mL portion after every hour. The reaction was further performed for 1 hour. The product was purified by silica gel column chromatography (hexane/ethyl acetate=1/1) and further by vacuum distillation to give a target compound (91% yield). $^1$H NMR (300 MHz, CDCl$_3$): δ 1.37 (t, J=7.2 Hz, 6H), 3.85 (s, 3H), 4.01-4.22 (m, 4H), 7.05-7.11 (m, 1H), 7.29-7.42 (m, 3H). $^{31}$P NMR (121 MHz, CDCl$_3$): δ 19.8 (s).

<Reaction 1-4-2>

[Chem. 15]

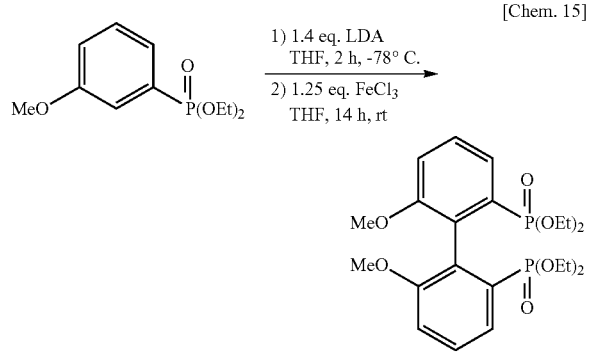

A 300 mL three-necked flask was thoroughly dried and was charged, in an inert gas atmosphere, with diisopropylamine (14.5 mL, 103 mmol) and THF (50 mL). The mixture was cooled to −20° C. Subsequently, 1.63 M n-butyllithium (60 mL, 98 mmol) was added dropwise over a period of about 1 hour, and stirring was performed for 30 minutes. The mixture was then cooled to −78° C., and a THF (90 mL) solution of diethyl (3-methoxyphenyl)phosphate (17.6 g, 72.0 mmol) synthesized in Reaction 1-4-1 was added dropwise over a period of about 1 hour, and the reaction was carried out for 2 hours. Further, a THF (90 mL) solution of iron (III) chloride (14.7 g, 90.0 mmol) was added to the reactor, and the reaction was carried out at room temperature for 14 hours. The solvent was distilled away. The residue was dissolved in dichloromethane, and the solution was combined with an aqueous sodium hydroxide solution. The mixture was filtered through Celite. The organic matter was extracted with dichloromethane. The extracted phase was washed with a saturated aqueous sodium chloride solution, and was concentrated. The concentrate was washed with Et$_2$O and purified by silica gel column chromatography (ethyl acetate/methanol=10/1), and impurities were removed with Florisil. Thus, a target compound was obtained (42% yield). $^1$H NMR (300 MHz, CDCl$_3$): δ 1.12 (t, J=8.3 Hz, 6H), 1.16 (t, J=8.3 Hz, 6H), 3.71 (s, 3H), 3.77-3.93 (m, 8H), 7.10 (d, J=8.1 Hz, 2H), 7.29-7.42 (m, 3H), 7.56 (ddd, J=1.2, 7.8, 13.5 Hz, 2H). $^{31}$P NMR (121 MHz, CDCl$_3$): δ 18.6 (s).

<Reaction 1-4-3>

[Chem. 16]

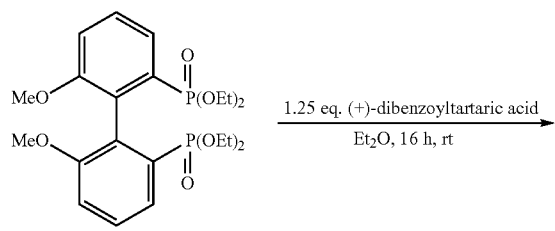

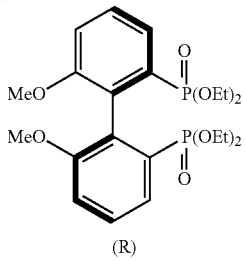

Diethyl [6'-(diethoxyphosphonyl)-6,2'-dimethoxy-biphenyl-2-yl]-2-phosphate (7.81 g, 16.1 mmol) synthesized in Reaction 1-4-2 and (+)-dibenzoyltartaric acid (6.91 g, 19.3 mmol) were added to a 1000 mL recovery flask and were mixed with each other sufficiently. Next, Et$_2$O (500 mL) was added, and the mixture was stirred for 16 hours. The solid that had been precipitated was separated by filtration, washed with Et$_2$O, and dissolved in dichloromethane. The resultant solution was washed with a saturated aqueous sodium hydrogencarbonate solution. The organic phase was concentrated to give a target compound (47% yield, (R)-isomer, >99% ee). HPLC (Daicel Chiralcel OD-H, Hexane/i-PrOH=20/1, flow rate=1.0 mL/min); detected at 280 nm; $t_R$=21.6 min ((R)-isomer), $t_R$=25.2 min ((S)-isomer).

<Reaction 1-4-4>

[Chem. 17]

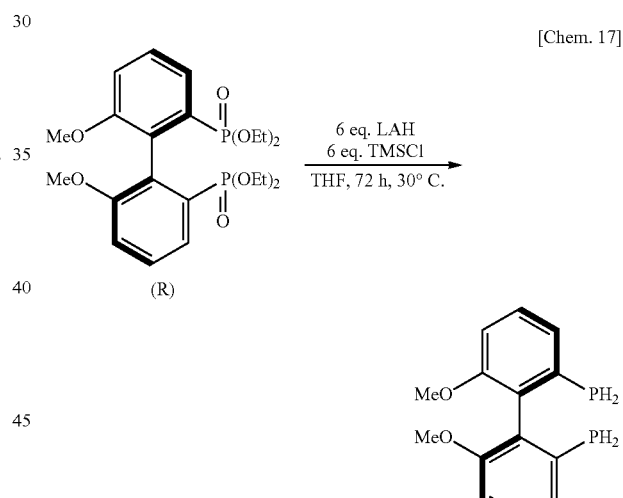

A 20 mL Schlenk tube was thoroughly dried and was charged, in an inert gas atmosphere, with lithium aluminum hydride (190 mg, 4.8 mmol) and THF (3 mL). The mixture was cooled to −78° C. Trimethylsilane chloride (0.61 mL, 4.8 mmol) was added dropwise over a period of about 5 minutes, and stirring was performed for 15 minutes. The mixture was then stirred at room temperature for 2 hours and was cooled to −30° C. A THF (3 mL) solution of diethyl (R)-[6'-(diethoxyphosphonyl)-6,2'-dimethoxybiphenyl-2-yl]-2-phosphate (390 mg, 0.8 mmol) was added dropwise over a period of about 10 minutes, and the reaction was carried out at 30° C. for 3 days. Deaerated water (0.8 mL) was added. After the generation of hydrogen ceased, a deaerated 30% aqueous sodium hydroxide solution (2.4 mL) and deaerated THF (10 mL) were added. The organic phase was transferred to another reactor with a cannula. Celite was added to the residue remaining in the Schlenk tube and the viscosity was reduced. The organic matter was extracted with THF. The extracted organic phase was washed with a deaerated saturated aqueous sodium chloride solution. After Et$_2$O (10 mL) was added, the aqueous phase was removed with a cannula. The residual organic phase was dried by the addition of sodium sulfate, and the solvent was distilled away. Thus, a target compound was obtained (95% yield). $^1$H NMR (300 MHz, CDCl$_3$): δ 3.57 (d, J$_{P-H}$=205 Hz, 4H), 3.73 (s, 6H), 6.93 (d, J=7.8 Hz, 2H), 7.23-7.31 (m, 4H). $^{31}$P NMR (121 MHz, CDCl$_3$): δ −127.2 (s).

<Reaction 1-4-5>

[Chem. 18]

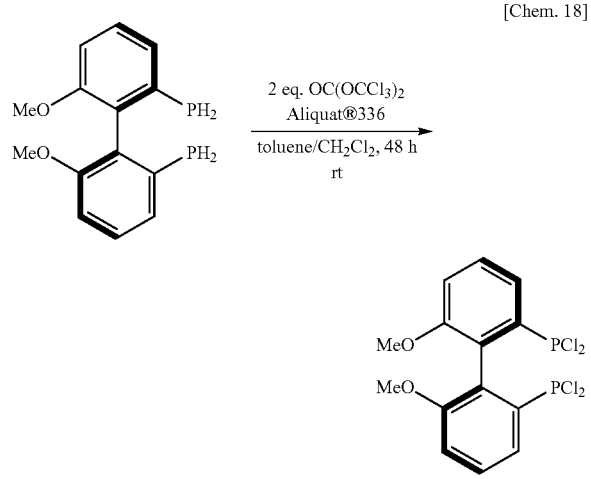

A 30 mL pressure resistant test tube was thoroughly dried and was charged with triphosgene (480 mg, 1.62 mmol). A toluene solution (3 mL) of Aliquat (registered trademark) 336 (38 mg, 0.094 mmol) was added, and the test tube was quickly closed. The mixture was vigorously stirred at 35° C. for 2 days. Thereafter, this reaction solution and a methylene chloride solution (6 mL) of (R)-[6,6'-dimethoxy(1,1'-biphenyl)-2,2'-diyl]bisphosphine (224 mg, 0.804 mmol) synthesized in Reaction 1-4-4 were cooled to −78° C. With use of a cannula, the toluene solution was mixed to the methylene chloride solution. The mixture was gradually brought to room temperature and was stirred for another 2 days. The solvent was distilled away, and a mixture of a target compound and Aliquat (registered trademark) was obtained. The mixture was subjected to Reaction 1-4-6 without removing Aliquat (registered trademark) 336. $^1$H NMR (300 MHz, CDCl$_3$): δ 3.77 (s, 6H), 7.11 (d, J=8.4 Hz, 2H), 7.63 (m, 2H), 7.86 (d, J=8.1 H, 2H). $^{31}$P NMR (121 MHz, CDCl$_3$): δ 158.1 (s).

<Reaction 1-4-6>

[Chem. 19]

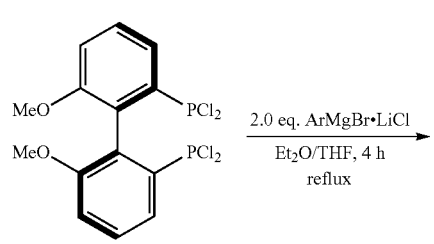

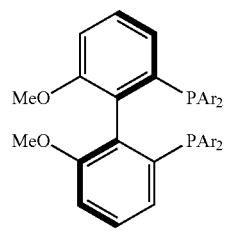

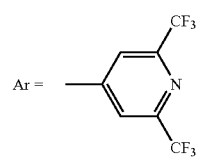

A thoroughly dried 50 mL two-necked recovery flask was charged with magnesium turnings (389 mg, 16.0 mmol) and lithium chloride (339 mg, 8.00 mmol). In an inert gas atmosphere, Et$_2$O (20 mL) was added. Next, a hexane solution of DAIBAL-H (1 M, 100 μL, 0.100 mmol) was added dropwise, and the mixture was stirred for 5 minutes. Thereafter, 4-bromo-2,6-bis(trifluoromethyl)pyridine (1.88 g, 6.40 mmol) was added, and the mixture was stirred for 1 hour. Subsequently, the mixture was added dropwise to a THF solution (1 mL) of (R)-[6,6'-dimethoxy(1,1'-biphenyl)-2,2'-diyl]phosphonous dichloride synthesized in Reaction 1-4-5 over a period of about 5 minutes. The reaction was carried out under reflux for 4 hours. The reaction was then terminated by the addition of a saturated aqueous ammonium chloride solution, and Et$_2$O and THF were distilled away. The residue was dissolved in ethyl acetate to perform extraction. The extracted phase was washed with a saturated aqueous sodium chloride solution, filtered through Celite, and concentrated to dryness. The product was purified by silica gel column chromatography (hexane/acetone=3/1) to give a target compound (52% yield (2 steps from Reaction 1-4-5)). $^1$H NMR (400 MHz, acetone-d$_6$): δ 3.72 (s, 6H), 7.16-7.19 (m, 2H), 7.38 (d, J=8.0 Hz, 2H), 7.86 (t, J=8.0 Hz, 2H), 7.89-7.91 (m, 4H), 8.15-8.17 (m, 4H). $^{13}$C NMR (100 MHz, acetone-d$_6$): δ 55.0, 114.2, 120.5 (q, $^1$J$_{F-C}$=274.5 Hz), 120.8 (q, $^1$J$_{F-C}$=274.4 Hz), 125.8-126.1 (m), 127.0-127.2 (m), 131.3, 132.5, 133.6-134.2 (m), 146.8-148.1 (m), 151.5-152.3 (m), 157.5-157.7 (m). $^{19}$F NMR (376 MHz, acetone-d$_6$): δ −64.9 (s, 12F), −64.5 (s, 12F). $^{31}$P NMR (162 MHz, acetone-d$_6$): δ −6.0 (s). IR (KBr): 3422, 3082, 2949, 2845, 1591, 1570, 1464, 1362, 1283, 1204, 1155, 1126, 1043, 891, 854, 718, 696, 625 cm$^{-1}$. Anal. calcd. for C$_{42}$H$_{20}$F$_{24}$N$_4$O$_2$P$_2$: C, 44.62; H, 1.78; N, 4.85. Found: C, 44.66; H, 1.94; N, 4.96. [α]$_D^{16.4}$=+33.9° (c 0.93, CHCl$_3$).

Example 1-5

[Chem. 20]

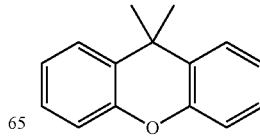

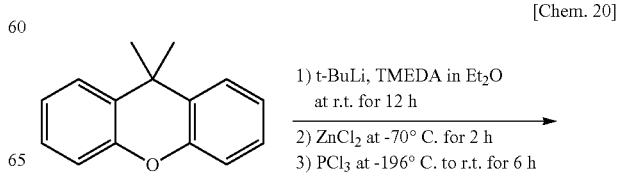

1) t-BuLi, TMEDA in Et$_2$O at r.t. for 12 h
2) ZnCl$_2$ at −70° C. for 2 h
3) PCl$_3$ at −196° C. to r.t. for 6 h -continued

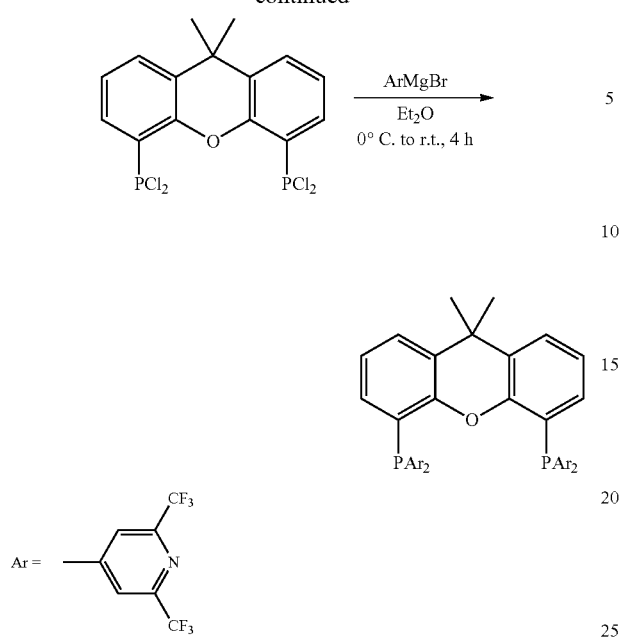

<Reaction 1-5-1>

<Reaction 1-5-2>

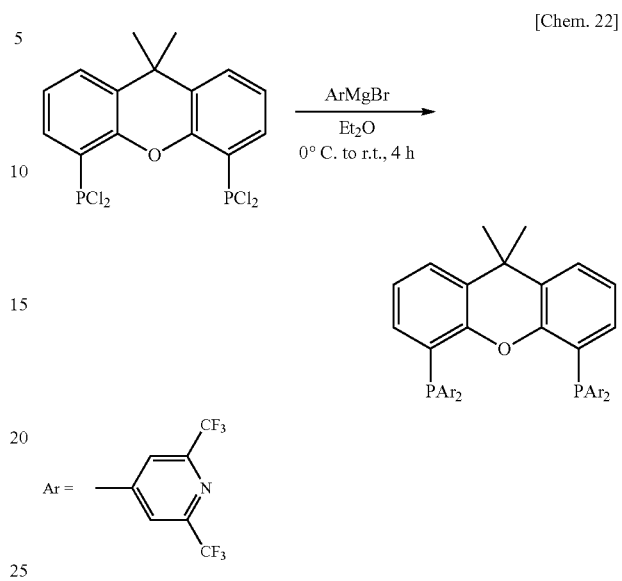

A 50 mL Schlenk tube was charged with 9,9-dimethylxanthene (177 mg, 0.808 mmol), tetramethylethylene diamine (0.0.50 mL, 3.2 mmol) and Et$_2$O (11 mL). The mixture was cooled to 0° C. in an ice bath, and t-BuLi (1.55 M in petane, 2.1 mL, 3.2 mmol) was added thereto dropwise. The resultant mixture was stirred at room temperature for 24 hours and was cooled to −70° C. in an ethanol bath. A Et$_2$O solution of zinc chloride (0.66 M, 3.1 mL, 2.0 mmol) was added dropwise. After stirring was performed at −70° C. for 2 hours, the reaction liquid was frozen by being immersed in a liquid nitrogen bath. PCl$_3$ (4.5 mL, 53 mmol) was added dropwise to the frozen reaction liquid, and the reactor was immersed in an ethanol bath at −70° C. The reaction liquid was stirred while increasing the temperature of the ethanol bath to room temperature over a period of 10 hours. The solvent was distilled away, and a light yellow crude product was obtained. The crude product was subjected to the next reaction without purification. $^1$H NMR (300 MHz, CDCl$_3$): δ 1.14 (t, J=7.0 Hz, 6H), 3.10-3.22 (m, 8H). $^{31}$P NMR (121 MHz, CDCl$_3$): δ 160.2 (s).

A thoroughly dried 50 mL two-necked recovery flask was charged with magnesium turnings (334 mg, 13.7 mmol) and lithium chloride (290 mg, 6.84 mmol). In an inert gas atmosphere, Et$_2$O (11 mL) was added. Next, a hexane solution of DAIBAL-H (1 M, 85 µL, 0.085 mmol) was added dropwise, and the mixture was stirred for 5 minutes. Thereafter, 4-bromo-2,6-bis(trifluoromethyl)pyridine (1.60 g, 5.44 mmol) was added, and the mixture was stirred for 1 hour. Further, a THF solution (2 mL) of 9,9-dimethylxanthene-4,5-diyl-bisphosphonous dichloride synthesized in Reaction 1-5-1 was added dropwise, and the mixture was stirred for 17 hours. After the addition of saturated aqueous ammonium chloride, the solvent was distilled away. The residue was extracted with ethyl acetate. The product was subjected to silica gel column (hexane/acetone=3/1) and recrystallization with acetone-hexane. Thus, a white solid (69.0 mg, 8%) was obtained. $^1$H NMR (400 MHz, CDCl$_3$): δ 1.72 (s, 6H), 6.43-6.45 (m, 2H), 7.26 (dd, J=8.0 Hz, J=8.0 Hz, 2H), 7.61-7.65 (m, 8H), 7.70 (dd, J=8.0 Hz, J=1.2 Hz, 2H). $^{19}$F NMR (376 MHz, CDCl$_3$): δ −69.2 (s). $^{31}$P NMR (162 MHz, CDCl$_3$): δ −14.8 (s). IR (KBr): 3074, 2978, 2932, 2872, 1593, 1452, 1412, 1364, 1283, 1246, 1202, 1151, 1126, 999, 897, 854, 791, 745, 718, 696, 623, 532 cm$^{-1}$. Anal. calcd. for C$_{45}$H$_{26}$F$_{24}$N$_4$OP$_2$: C, 45.84; H, 1.79; N, 4.97. Found: C, 46.03; H, 1.98; N, 5.08.

Example 2-1

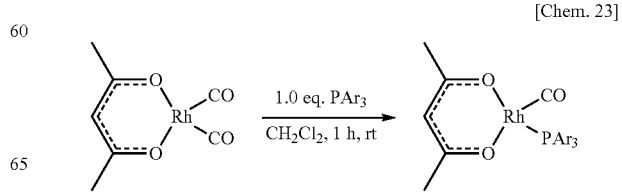

-continued

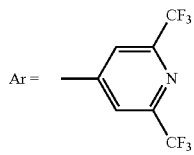

A 25 mL two-necked flask was thoroughly dried and was charged with (acetylacetonato)dicarbonyl rhodium (I) (22.0 mg, 0.0853 mmol) and tris[2,6-bis(trifluoromethyl)-pyridyl]phosphine (57.4 mg, 0.0853 mmol). In an inert gas atmosphere, dichloromethane (5 mL) was added, and the mixture was stirred for 1 hour. The reaction liquid was passed through cotton to remove solids, and the solvent was distilled away. The product was subjected to recrystallization (dichloromethane/hexane) to give a target compound (21% yield). $^1$H NMR (300 MHz, CDCl$_3$): δ 1.70 (s, 3H), 2.20 (s, 3H), 5.63 (s, 1H), 8.05 (d, J=10.8 Hz, 6H). $^{19}$F NMR (282 MHz, CDCl$_3$): δ −69.1 (s). $^{31}$P NMR (121 MHz, CDCl$_3$): δ 52.6 (d, $^1J_{Rh-P}$=188.0 Hz). IR (CH$_2$Cl$_2$): 3071, 2007, 1204, 1162, 1128, 896 cm$^{-1}$. Anal. calc. for C$_{27}$H$_{13}$F$_{18}$RhN$_3$O$_3$P: C, 35.90; H, 1.45; N, 4.65. Found: C, 36.20; H, 1.66; N, 4.89.

Example 2-2

[Chem. 24]

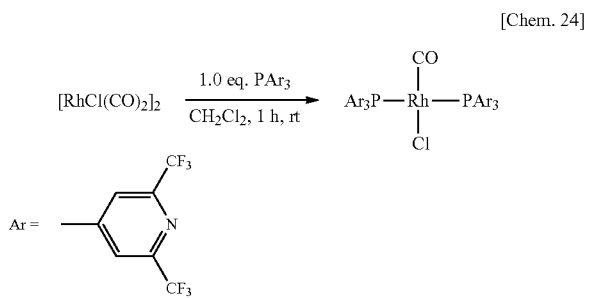

A 20 mL Schlenk tube was thoroughly dried and was charged with μ-dichlorotetracarbonyl rhodium (I) (4.30 mg, 0.0111 mmol) and tris[2,6-bis(trifluoromethyl)-pyridyl]phosphine (30.0 mg, 0.0446 mmol). In an inert gas atmosphere, dichloromethane (1.5 mL) was added, and the mixture was stirred for 1 hour. The reaction liquid was passed through cotton to remove solids, and the solvent was distilled away. The product was subjected to recrystallization (dichloromethane/benzene) to give a target compound (60% yield). $^1$H NMR (300 MHz, acetone-d$_6$): δ 8.70-8.82 (m). $^{19}$F NMR (282 MHz, acetone-d$_6$): δ −65.0 (s). $^{31}$P NMR (121 MHz, acetone-d$_6$): δ 39.4 (d, $^1J_{Rh-P}$=139.2 Hz). IR (CH$_2$Cl$_2$): 3051, 2951, 2017, 1363, 1281, 1205, 1166, 1129, 895 cm$^{-1}$. M.p.=230° C. (dec.).

<Measurement of Electron-Withdrawing Power>

Figure 3:
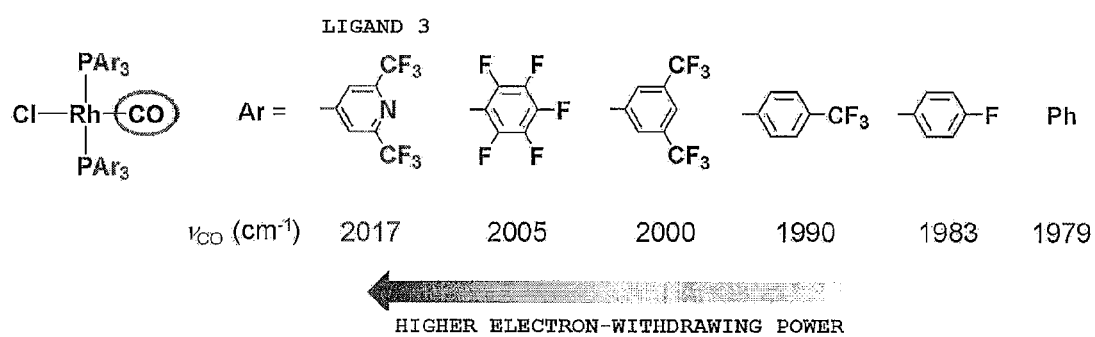
FIG. 3 is a view illustrating the results of measurement of electron-withdrawing power of a ligand in Example 2-2.

The electron-withdrawing power was measured of the PAr$_3$ ligand 3 (see Example 1-1) and four types of known PAr$_3$ control ligands having a fluorinated aromatic ring (see Patent Literature 1) or a benzene ring. Each ligand compound was reacted with the rhodium complex having carbonyl groups in the same manner as in Example 2-2 to form a complex, and the carbonyl stretching vibration of the complex was examined. As a result, the ligand 3 induced a greater stretching vibration than by any of the control ligands (FIG. 3). This result indicated that the ligand 3 was highly electron-deficient.

Example 2-3

[Chem. 25]

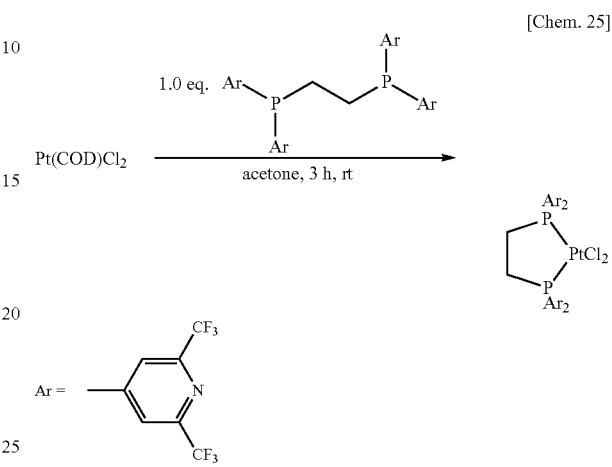

A 20 mL Schlenk tube was thoroughly dried and was charged with dichloro(1,5-cyclooctadiene)platinum (II) (10.5 mg, 0.0281 mmol) and bis[[2,6-bis(trifluoromethyl)-pyridyl]phosphino]ethane (26.5 mg, 0.0280 mmol). In an inert gas atmosphere, acetone (2 mL) was added, and the mixture was stirred for 3 hours. The solvent was distilled away, and the product was subjected to recrystallization (dichloromethane/hexane) to give a target compound (59% yield). $^1$H NMR (300 MHz, acetone-d$_6$): δ 3.80-3.90 (m, 4H), 8.80-8.87 (m, 8H). $^{19}$F NMR (282 MHz, acetone-d$_6$): δ −64.9 (s). $^{31}$P NMR (121 MHz, acetone-d$_6$): δ 49.6 (s w/Pt-satellites, $^1J_{Pt-P}$=3560 Hz). Anal. calc. for C$_{30}$H$_{12}$Cl$_2$F$_{24}$N$_4$P$_2$Pt: C, 29.72; H, 1.00; N, 4.62. Found: C, 29.76; H, 1.15; N, 4.57.

Example 2-4

[Chem. 26]

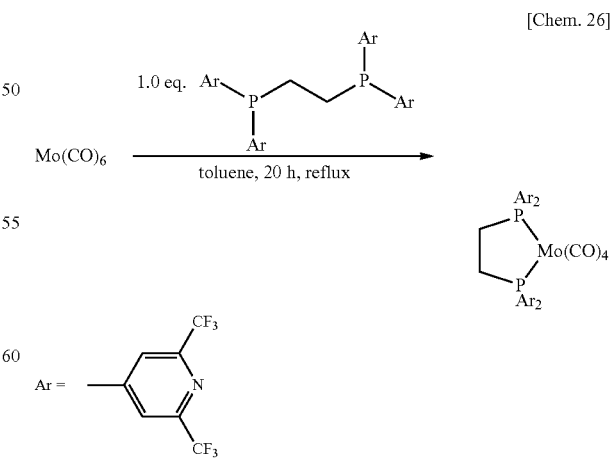

A 20 mL Schlenk tube was thoroughly dried and was charged with hexacarbonylmolybdenum (14.0 mg, 0.0530 mmol) and bis[[2,6-bis(trifluoromethyl)-pyridyl]phosphino]ethane (50.2 mg, 0.0530 mmol). In an inert gas atmosphere, toluene (0.5 mL) was added, and the mixture was refluxed for 20 hours. The solvent was distilled away, and the product was subjected to recrystallization (acetone/benzene) to give a target compound (77% yield). $^1$H NMR (300 MHz, acetone-$d_6$): δ 3.58-3.76 (m, 4H), 8.51 (d, J=9.6 Hz, 8H). $^{19}$F NMR (282 MHz, acetone-$d_6$): δ −64.6 (s). $^{31}$P NMR (121 MHz, acetone-$d_6$): δ 72.5 (s). IR (CH$_2$Cl$_2$): 3060, 3005, 2040.7, 1936, 1362, 1271, 1206, 1163, 1127, 897 cm$^{-1}$. Anal. calc. for C$_{34}$H$_{12}$F$_{24}$MoN$_4$O$_4$P$_2$: C, 35.38; H, 1.05; N, 4.85. Found: C, 35.00; H, 1.26; N, 4.75.

Example 2-5

Synthesis Scheme (Reactions 2-5-1 to 2-5-3 Described Below)

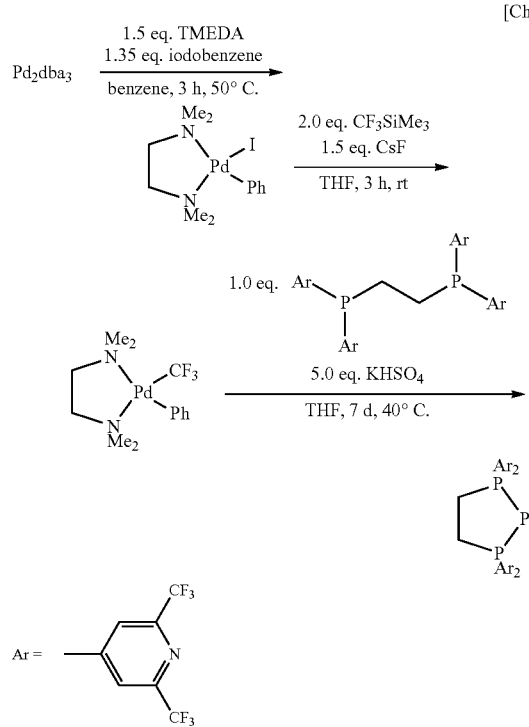

<Reaction 2-5-1>

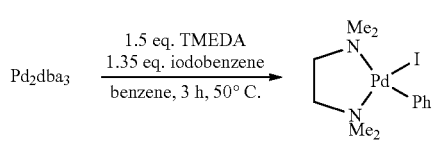

A 20 mL Schlenk tube was thoroughly dried and was charged with tris(dibenzylideneacetone)dipalladium (91.5 mg, 0.100 mmol). In an inert gas atmosphere, N,N,N',N'-tetramethyl-1,2-ethanediamine (45 μL, 0.30 mmol), iodobenzene (30 μL, 0.27 mmol) and benzene (1.5 mL) were added, and the mixture was stirred at 50° C. for 3 hours. The reaction liquid was filtered through Celite, and the solvent was distilled away. The product was then subjected to recrystalliza-tion (dichloromethane/Et$_2$O) to give a target compound (90% yield). $^1$H NMR (300 MHz, CDCl$_3$): δ 2.34 (s, 6H), 2.55-2.77 (m, 10H), 6.77-6.83 (m, 1H), 6.89-6.95 (m, 2H), 7.23-7.27 (m, 2H). $^{13}$C NMR (75 MHz, CDCl$_3$): δ 49.7, 49.9, 58.2, 62.1, 121.7, 126.5, 136.4, 144.5.

<Reaction 2-5-2>

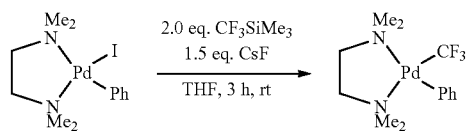

A 20 mL Schlenk tube was thoroughly dried and was charged with iodophenyl(N,N,N',N'-tetramethyl-1,2-ethanediamine) palladium (80.0 mg, 0.188 mmol) and cesium fluoride (42.8 mg, 0.282 mmol). In an inert gas atmosphere, trifluoromethyltrimethylsilane (56 ml, 0.38 mmol) and THF (1 mL) were added, and the mixture was stirred for 3 hours. The reaction liquid was filtered through Celite, and the solvent was distilled away. The product was then subjected to recrystallization (dichloromethane/Et$_2$O) to give a target compound (67% yield). $^1$H NMR (300 MHz, CDCl$_3$): δ 2.23 (s, 6H), 2.55-2.70 (m, 10H), 6.90-7.00 (m, 3H), 7.46-7.49 (m, 2H). $^{13}$C NMR (75 MHz, CDCl$_3$): δ 49.7, 49.9, 58.2, 62.1, 121.7, 126.5, 136.4, 144.5. $^{19}$F NMR (282 MHz, CDCl$_3$): δ −22.6 (s). IR (KBr): 3051, 2975, 2899, 2842, 1566, 1463, 1093, 1061, 1021, 979, 962, 804, 746, 706 cm$^{-1}$.

<Reaction 2-5-3>

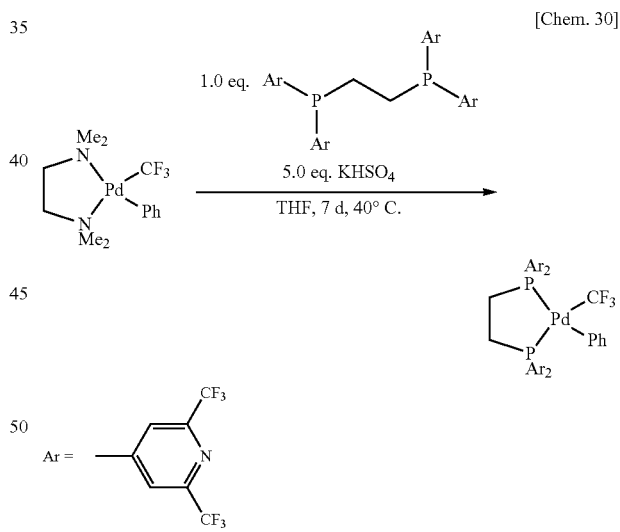

A 20 mL Schlenk tube was thoroughly dried and was charged with iodo(N,N,N',N'-tetramethyl-1,2-ethanediamine) (trifluoromethyl)palladium (19.9 mg, 0.0540 mmol), potassium hydrogensulfate (42.8 mg, 0.282 mmol) and bis[[2,6-bis(trifluoromethyl)-pyridyl]phosphino]ethane (51.1 mg, 0.0540 mmol). In an inert gas atmosphere, THF (1 mL) was added, and the mixture was stirred at 40° C. for 7 days. The reaction liquid was filtered through Celite, and the solvent was distilled away. The product was then subjected to recrystallization (dichloromethane/hexane) to give a target compound (25% yield). $^1$H NMR (300 MHz, acetone-$d_6$): δ 3.77-3.95 (m, 2H), 4.03-4.21 (m, 2H), 7.20-7.33 (m, 3H), 7.57-7.62 (m, 2H), 8.66 (d, J=10.1 Hz, 4H), 9.12 (d, J=10.1 Hz, 4H). $^{19}$F NMR (282 MHz, acetone-d$_6$): δ −64.5 (s, 12F), −64.4 (s, 12F), −12.2 (dd, J$_{F-P}$=52.1 Hz, J$_{F-P}$=18.4 Hz, 3F). $^{31}$P NMR (121 MHz, acetone-d$_6$): δ 45.4-45.7 (m), 49.2-50.3 (m).

Example 2-6

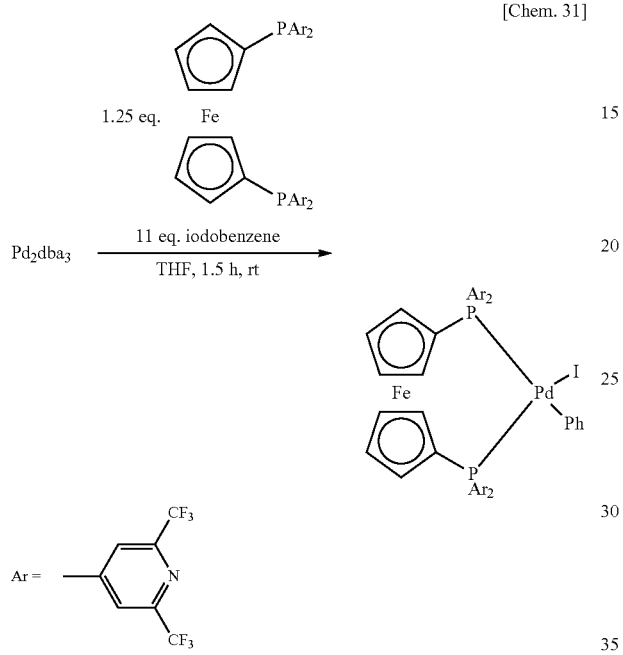

A 20 mL Schlenk tube was thoroughly dried and was charged with tris(dibenzylideneacetone)dipalladium (91.5 mg, 0.100 mmol) and 1,1'-bis[bis[2,6-bis(trifluoromethyl)-pyridyl]phosphino]ferrocene (276 mg, 0.250 mmol). THF (1.5 mL) was added, and the mixture was stirred for 1.5 hours. The reaction liquid was filtered through Celite, and the solvent was distilled away. The product was then subjected to recrystallization (dichloromethane/Et$_2$O) to give a target compound (68% yield). $^1$H NMR (300 MHz, CDCl$_3$): δ 4.30-4.33 (m, 2H), 4.60-4.62 (m, 2H), 4.94 (s), 5.30-5.33 (m, 2H), 6.44-6.55 (m, 1H), 6.54-6.60 (m, 2H), 6.94-6.70 (m, 2H), 8.21 (d, J=10.5 Hz, 4H), 8.90 (d, J=10.5 Hz, 4H). $^{19}$F NMR (282 MHz, CDCl$_3$): δ −64.9 (s, 12F), −64.8 (s, 12F). $^{31}$P NMR (121 MHz, CDCl$_3$): δ 15.9 (d, $^2$J$_{P-P}$=35.6 Hz), 30.8 (d, $^2$J$_{P-P}$=35.6 Hz).

Example 2-7

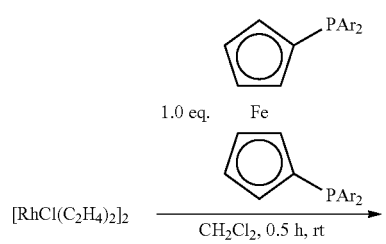

[Chem. 32]

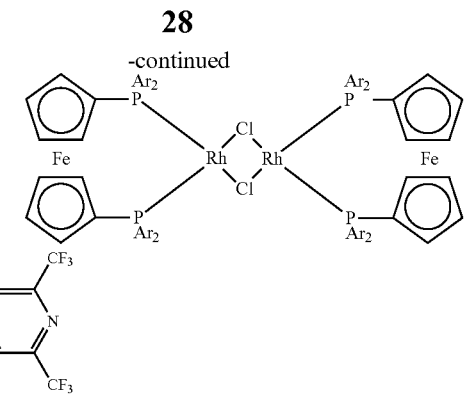

[Chem. 31]

A 20 mL Schlenk tube was thoroughly dried and was charged with μ-dichlorotetraethylene dirhodium (I) (1.00 mg, 0.00257 mmol) and 1,1'-bis[bis[2,6-bis(trifluoromethyl)-pyridyl]phosphino]ferrocene (5.68 mg, 0.00515 mmol). In an inert gas atmosphere, dichloromethane (0.5 mL) was added, and the mixture was stirred for 30 minutes. Thus, a target compound was obtained. $^{19}$F NMR (282 MHz, CH$_2$Cl$_2$): δ −70.2 (s). $^{31}$P NMR (121 MHz, CH$_2$Cl$_2$): δ 53.3 (d, $^1$J$_{Rh-P}$=202.9 Hz).

Example 2-8

[Chem. 33]

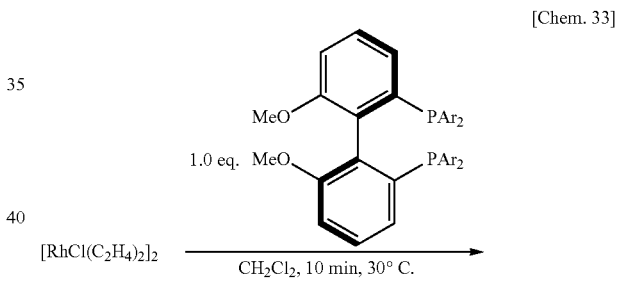

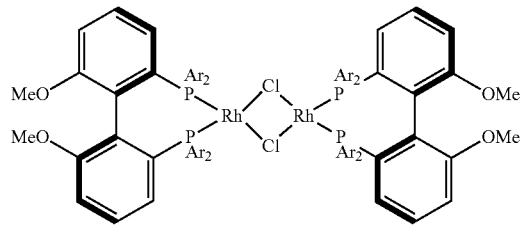

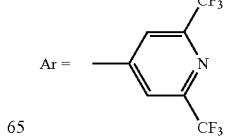

A 20 mL Schlenk tube was thoroughly dried and was charged with μ-dichlorotetraethylene dirhodium (I) (1.00 mg, 0.00257 mmol) and (R)-(6,6'-dimethoxybiphenyl-2,2'-diyl)bis[bis[2,6-bis(trifluoromethyl)-pyridyl]phosphine] (5.82 mg, 0.00515 mmol). In an inert gas atmosphere, dichloromethane (0.5 mL) was added, and the mixture was stirred at 30° C. for 10 minutes. Thus, a target compound was obtained. $^{19}$F NMR (282 MHz, CH$_2$Cl$_2$): δ −70.0 (s, 24F), −69.6 (s, 24F). $^{31}$P NMR (121 MHz, CH$_2$Cl$_2$): δ 49.1 (d, $^1J_{Rh-P}$=194.0 Hz).

Example 3-1

Stille Coupling Reaction

[Chem. 34]

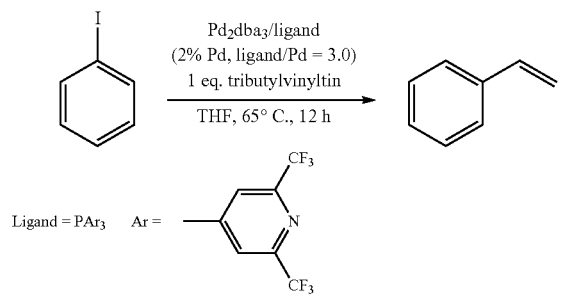

A 20 mL Schlenk tube was charged with tris(dibenzylideneacetone)dipalladium (1.5 mg, 1.6 mol) and tris[2,6-bis(trifluoromethyl)-pyridyl]phosphine (6.5 mg, 9.7 μmol). In an inert gas atmosphere, THF (1 mL) was added, and the mixture was stirred for 10 minutes. Thereafter, iodobenzene (18 μL, 0.16 mmol) and tributylvinyltin (48 μL, 0.16 mmol) were added. The mixture was stirred at 65° C. for 12 hours. A saturated aqueous sodium hydrogencarbonate solution was added, and the organic matter was extracted with ethyl acetate. The conversion was determined by H NMR (88% conv.). $^1$H NMR (300 MHz, CDCl$_3$): δ 5.25 (dd, J=10.8, 0.9 Hz, 1H), 5.75 (dd, J=17.4, 0.9 Hz, 1H), 6.72 (dd, J=17.4, 10.8 Hz, 1H), 7.25-7.36 (m, 3H), 7.40-7.43 (m, 2H).

<Comparison of Catalytic Activities>

As illustrated in Example 3-1, the palladium catalyst having the PAr$_3$ ligand (3) achieved 88% yield in the above Stille coupling reaction. This yield was higher than the yields reported in the same reaction catalyzed by palladium catalysts having a known phosphine (P(OPh)$_3$) or arsine (AsPh$_3$) ligand, and was higher than the yield obtained when the reaction in Example 3-1 was catalyzed by a known phosphine ligand. That is, the ligand (3) achieved a higher catalytic activity than conventional ligands of the same type (Table 1). This result is ascribed to the markedly strong electron-withdrawing power of the ligand (3). However, in view of the fact that the P(C$_6$F$_5$)$_3$ ligand, which is one of the most electron-deficient conventional ligands, exhibited a very low catalytic activity as a result of the poor coordination power due to steric effects, the above result clearly shows that the good performance by the ligand (3) was attained not only by the electronic effects but also because the design focusing on the strong coordination to metals worked successfully.

TABLE 1

| Ligand | Yield of product | Remarks |
|---|---|---|
| PAr$_3$  Ar = (2,6-bis(CF$_3$)pyridyl) | 88% | Present invention |
| PAr$_3$  Ar = (3,5-bis(CF$_3$)phenyl) | 74% | |
| AsPH$_3$ | 73% | Conventional effective ligands in Stille coupling J. Am. Chem. Soc. 1991, 113, 9585. |
| P(OPh)$_3$ | 62% | |
| P(C$_6$F$_5$)$_3$ | 6% | |
| PPh$_3$ | 6% | |

Example 3-2

Asymmetric Arylation of Imine

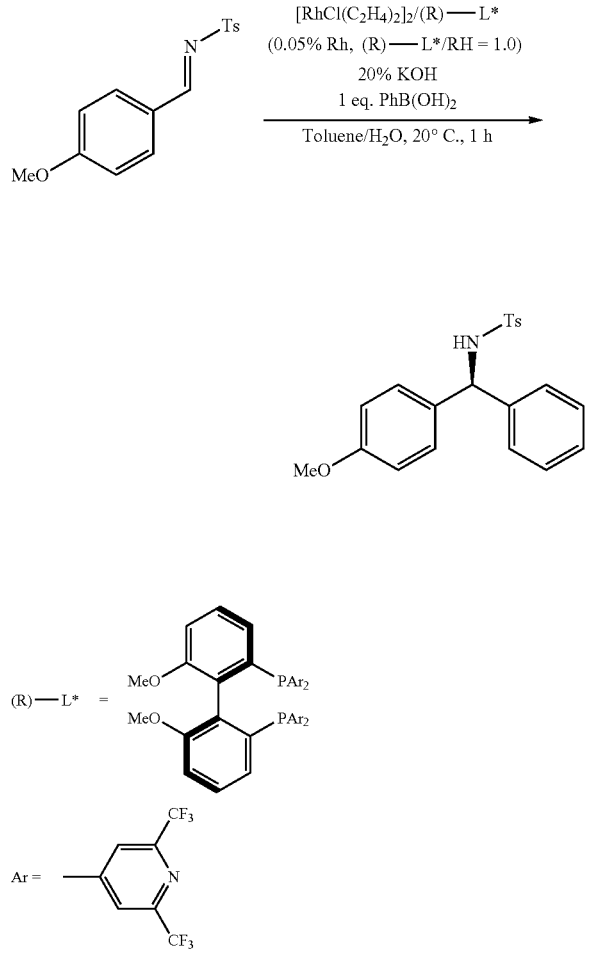

A 20 mL Schlenk tube was thoroughly dried and was charged with μ-dichlorotetraethylene dirhodium (I) (50.5 μg, 0.130 μmol) and (R)-(6,6'-dimethoxybiphenyl-2,2'-diyl) bis[bis[2,6-bis(trifluoromethyl)-pyridyl]phosphine] (294 μg, 0.260 μmol). In an inert gas atmosphere, dichloromethane (0.2 mL) was added, and the mixture was stirred for 15 minutes. The solvent was distilled away. Subsequently, 4-methoxybenzaldehyde tosylimine (151 mg, 0.520 mmol), phenylboronic acid (63.4 mg, 0.520 mmol) and potassium hydroxide (5.84 mg, 0.104 mmol) were added. Further, toluene (0.5 mL) and water (0.25 mL) were added, and the mixture was stirred at 20° C. for 1 hour. A saturated aqueous sodium hydrogencarbonate solution was added, and the organic matter was extracted with ethyl acetate. The product was purified by silica gel column chromatography (hexane/ethyl acetate=1/1) to give a target compound (98% yield, (S)-isomer, 98% ee). $^1$H NMR (400 MHz, CDCl$_3$): δ 2.38 (s, 3H), 3.75 (s, 3H), 5.01 (d, J=6.8 Hz, 1H), 5.52 (d, J=6.8 Hz, 1H), 6.73 (d, J=8.8 Hz, 2H), 6.99 (d, J=8.8 Hz, 2H), 7.09-7.21 (m, 7H), 7.56 (d, J=8.0 Hz, 2H). $[\alpha]_D^{26.7}$=−19.7° (c 1.0, CHCl$_3$). HPLC (Daicel Chiralcel OD-H, Hexane/i-PrOH=70/30, flow rate=0.7 mL/min); detected at 230 nm; $t_R$=11.0 min ((S)-isomer), $t_R$=16.9 min ((R)-isomer).

<Comparison of Catalytic Activities>

In the asymmetric acylation of an imine similar to that in Example 3-2, as little as 0.05% of the rhodium complex (17) having the chiral ligand (10) allowed the reaction to complete in 1 hour at 30° C., and the reaction afforded an optically active amine having an enantiomeric excess of 98% (Table 2). While more than ten techniques have been reported for reactions catalyzed by transition metal catalysts similar to the present reaction, most of such techniques involve a 3% or more catalyst and require a reaction time of several hours to several tens of hours. In contrast, the novel rhodium complex (17) affords an optically active compound in a very short time with a markedly small amount of the catalyst. Thus, the technique according to the invention can be expected to provide an effective and efficient method for the synthesis of optically active amines.

TABLE 2

| | Amount of Rh catalyst | Reaction conditions Temp. | Time | Yield | ee |
|---|---|---|---|---|---|
| Present invention (Ex. 3-2) | 0.05% | 20° C. | 1 h | 98% | 98% |
| G.-Q. Lin Org. Lett. 2010, 17, 3820. | 3% | 55° C. | >5 h | 99% | 95% |
| A. J. Carnell Angew. Chem. Int. Ed. 2010, 49, 2750. | 1.5% | r.t. | 3 h | 91% | 94% |
| T. Hayashi Chem. Comunn. 2009, 4815. | 0.3% | 60° C. | 12 h | 96% | 99% |
| N. Miyaura Adv. Synth. Catal. 2009, 351, 260. | 3% | 50° C. | 16 h | 88% | 94% |
| M. Shi Org. Lett. 2009, 875. | 3% | 4° C. | >12 h | 99% | 88% |
| G.-Q. Lin J. Am. Chem. Soc. 2007, 129, 5336. | 6% | 55° C. | >4 h | 99% | 99% |
| Q.-L. Zhou Org. Lett. 2006, 8, 2567. | 3% | 35° C. | 20 h | 65% | 93% |
| T. Hayashi J. Am. Chem. Soc. 2004, 126, 13584. | 3% | 60° C. | 6 h | 96% | 99% |

Further, Table 3 compares hourly catalytic activities of the invention and of known chiral phosphine ligands described in Patent Literature 1 under the same conditions as in Example 3-2. At room temperature, the known chiral phosphine ligands show a turnover frequency (TOF) value of 620 per hour at a maximum while the chiral phosphine ligand (10) of the invention has as high a TOF value of 1960. Thus, the comparison clearly shows the high activity of the inventive ligands as well as the superiority as ligands of the phosphines having bistrifluoromethyl-pyridyl groups which are highly electron-deficient and are nonbulky.

TABLE 3

| Ligand | | TOF of catalyst | Remarks |
|---|---|---|---|
| (R)—L* = 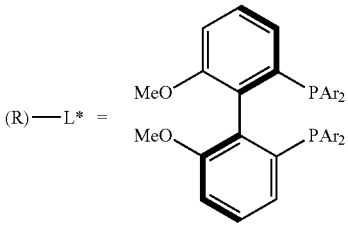 | Ar = 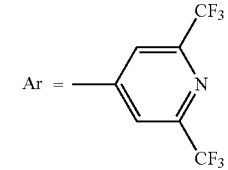 | 1960 h⁻¹ | Present invention |
| | Ar = 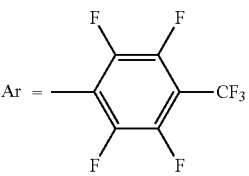 | 0 h⁻¹ | Patent Literature 1 (JP-A-2010-173958) |
| | Ar = 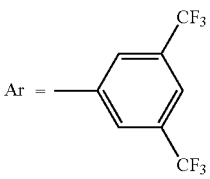 | 620 h⁻¹ | |
| | Ar = 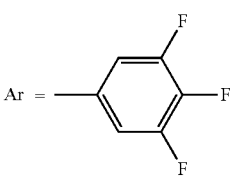 | 510 h⁻¹ | |
| (R)—BINAP | | 0 h⁻¹ | |

The invention claimed is:

1. A compound represented by General Formula (1) or (2) and having a total of 15 to 110 carbon atoms:

$$R^1R^2R^3A \quad (1)$$

$$R^1R^2A-Y-AR^3R^4 \quad (2)$$

wherein A is phosphorus or arsenic; $R^1$, $R^2$, $R^3$ and $R^4$ are each independently a pyridyl group having optionally different electron-withdrawing groups bonded to both positions meta to the atom A as well as hydrogen atoms bonded to both positions ortho to the atom A; and Y is a divalent group derived from a $C_{2-20}$, optionally substituted and optionally heteroatom-containing, aliphatic, alicyclic or aromatic compound or from ferrocene, and provided that the nitrogen atom in the pyridine ring has the lowest number (1-position), the positions meta to the atom A are the 2-position and the 6-position, and the optionally different electron-withdrawing groups are bonded to both the 2-position and the 6-position, and the positions ortho to the atom A are the 3-position and the 5-position, and hydrogen atoms are bonded to both the 3-position and the 5-position.

2. The compound according to claim 1, wherein the electron-withdrawing group is at least one selected from the group consisting of a perhaloalkyl group having 1 to 4 carbon atoms, a halogen, nitro group, cyano group, pentafluorophenyl group, tetrafluoropyridyl group, heptafluorotolyl group, 2,6-ditrifluoromethylpyridyl group and 3,5-ditrifluoromethylphenyl group.

3. The compound according to claim 2, wherein the perhaloalkyl group having 1 to 4 carbon atoms is at least one selected from the group consisting of a perfluoroalkyl group, a perchloroalkyl group and a perbromoalkyl group each having 1 to 4 carbon atoms.

4. The compound according to claim 3, wherein the perfluoroalkyl group having 1 to 4 carbon atoms is at least one selected from the group consisting of trifluoromethyl group, pentafluoroethyl group, heptafluoropropyl group and nanafluorobutyl group.

5. The compound according to claim 2, wherein the halogen is at least one selected from the group consisting of fluorine, chlorine, bromine and iodine.

6. The compound according to claim 1, which is tri[2,6-bis(trifluoromethyl)-4-pyridyl]phosphine.

7. The compound according to claim 1, which is tri[2,6-bispentafluoroethyl-4-pyridyl]phosphine.

8. The compound according to claim 1, which is tri[2,6-bisheptafluoropropyl-4-pyridyl]phosphine.

9. The compound according to claim 1, which is tri[2,6-bisnanafluorobutyl-4-pyridyl]phosphine.

10. The compound according to claim 1, which is tri[2,6-difluoro-4-pyridyl]phosphine.

11. The compound according to claim 1, which is tri[2,6-dinitro-4-pyridyl]phosphine.

12. The compound according to claim 1, which is tri[2,6-dicyano-4-pyridyl]phosphine.

13. The compound according to claim 1, which is represented by Formula (4), (5) or (6) below:

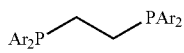

(4)

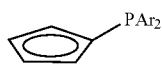

(5)

(6)

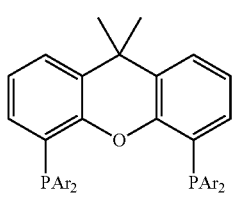

(wherein Ar is 2,6-bistrifluoromethyl-4-pyridyl group).

14. The compound according to claim 1, which is represented by General Formula (7) below:

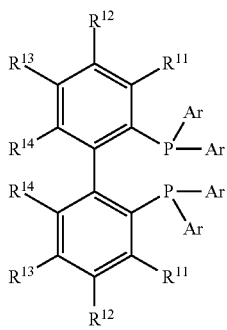

(7)

(wherein $R^{11}$, $R^{12}$ and $R^{13}$ are each independently a hydrogen atom, a halogen atom, an alkyl group having 1 to 6 carbon atoms, an alkoxy group having 1 to 6 carbon atoms, a fluorinated alkyl group having 1 to 10 carbon atoms, or a fluorinated alkoxy group having 1 to 10 carbon atoms; $R^{14}$ is an alkyl group having 1 to 6 carbon atoms, a fluorinated alkyl group having 1 to 10 carbon atoms, an alkoxy group having 1 to 6 carbon atoms, or a fluorinated alkoxy group having 1 to 10 carbon atoms; and $R^{11}$, $R^{12}$, $R^{13}$ and $R^{14}$ on the same benzene ring may be linked to one another to form a ring).

15. The compound according to claim 14, which is an axially chiral compound represented by Formula (10), (11), (12) or (13) below:

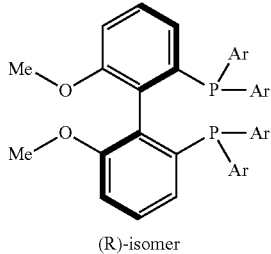

(10)

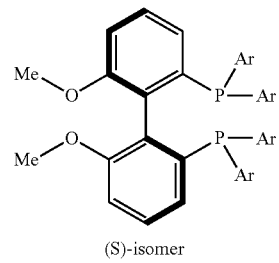

(11)

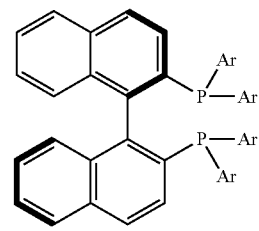

(12)

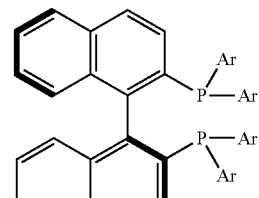

(13)

(wherein Me is methyl group and Ar is 2,6-bistrifluoromethyl-4-pyridyl group).

16. A ligand comprising the compound described in claim 1.

17. A transition metal complex in which the ligand described in claim 16 is coordinated to a transition metal having coordination capability.

18. The transition metal complex according to claim 17, wherein the transition metal having coordination capability is titanium, vanadium, manganese, iron, cobalt, nickel, copper, zirconium, niobium, molybdenum, ruthenium, rhodium, palladium, hafnium, tantalum, tungsten, rhenium, osmium, iridium, silver, gold or platinum.

19. A catalyst comprising the transition metal complex described in claim 17.

20. The catalyst according to claim 19, which is a chiral catalyst represented by Formula (17) below:

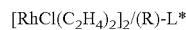

(17)

(wherein (R)-L* indicates a chiral bidentate ligand formed by an axially chiral compound represented by Formula (10)).

* * * * *

UNITED STATES PATENT AND TRADEMARK OFFICE
CERTIFICATE OF CORRECTION

| | | |
|---|---|---|
| PATENT NO. | : 8,779,133 B2 | Page 1 of 1 |
| APPLICATION NO. | : 13/985378 | |
| DATED | : July 15, 2014 | |
| INVENTOR(S) | : Korenaga et al. | |

It is certified that error appears in the above-identified patent and that said Letters Patent is hereby corrected as shown below:

On Title Page 2, Column 2, item [56] Other Publications, Line 10, delete "Electeron-Poor" and insert -- Electron-Poor --

In the Claims

Column 34, Lines 51-52, Claim 4, delete "nanafluorobutyl" and insert -- nonafluorobutyl --

Signed and Sealed this
Second Day of December, 2014

Michelle K. Lee
*Deputy Director of the United States Patent and Trademark Office*